(12) United States Patent
Kasmi

(10) Patent No.: US 10,229,492 B2
(45) Date of Patent: Mar. 12, 2019

(54) DETECTION OF BORDERS OF BENIGN AND MALIGNANT LESIONS INCLUDING MELANOMA AND BASAL CELL CARCINOMA USING A GEODESIC ACTIVE CONTOUR (GAC) TECHNIQUE

(71) Applicant: Stoecker & Associates, LLC, Rolla, MO (US)

(72) Inventor: Reda Kasmi, Bejaia (DZ)

(73) Assignee: Stoecker & Associates, LLC, Rolla, MO (US)

( * ) Notice: Subject to any disclaimer, the term of this patent is extended or adjusted under 35 U.S.C. 154(b) by 75 days.

(21) Appl. No.: 15/231,538

(22) Filed: Aug. 8, 2016

(65) Prior Publication Data
US 2017/0039704 A1    Feb. 9, 2017

Related U.S. Application Data

(60) Provisional application No. 62/202,682, filed on Aug. 7, 2015.

(51) Int. Cl.
*G06T 5/20*      (2006.01)
*G06T 7/00*      (2017.01)
(Continued)

(52) U.S. Cl.
CPC .......... *G06T 7/0012* (2013.01); *A61B 5/444* (2013.01); *G06T 5/002* (2013.01); *G06T 5/20* (2013.01);
(Continued)

(58) Field of Classification Search
CPC .......... G06T 2207/10024; G06T 2207/30096
See application file for complete search history.

(56) References Cited

U.S. PATENT DOCUMENTS

| | | | | |
|---|---|---|---|---|
| 5,982,953 A | * | 11/1999 | Yanagita | ............... G06F 19/321 348/580 |
| 7,282,723 B2 | * | 10/2007 | Schomacker | ........ A61B 5/0059 250/458.1 |

(Continued)

OTHER PUBLICATIONS

Anderson, R. Rox et al., The Optics of Human Skin, Department of Dermatology, Harvard Medical School, Massachusetts General Hospital, Boston, Massachusetts, U.S.A., The Journal of Investigative Dermatology, 77:13-19, 1981, vol. 77, No. 1, pp. 13-19.

(Continued)

*Primary Examiner* — Gandhi Thirugnanam
(74) *Attorney, Agent, or Firm* — Faegre Baker Daniels LLP

(57) ABSTRACT

A method for automatic segmentation of dermoscopy skin lesion images includes automating a Geodesic Active Contour (GAC) initialization to be sufficiently large to encompass the lesion yet lie near the actual lesion contour. In addition, a new image plane is found by transforming the original RGB image to a smoothed image that allows the GAC to move without sticking on the minimum local energy. This method can eliminate the need for separate hair or noise removal algorithms. The method may include extraction of designated color planes to improve the initial contour and to automatically correct false segmentations. The method includes an algorithm to correct false protuberances and/or false inlets that may be present in the GAC border. A method is given to increase likelihood of including more actual lesion area. The method yields multiple border choices which may be presented to a classifier for optimal border selection.

20 Claims, 19 Drawing Sheets
(17 of 19 Drawing Sheet(s) Filed in Color)

(51) Int. Cl.
G06T 5/00 (2006.01)
A61B 5/00 (2006.01)
G06T 7/11 (2017.01)
G06T 7/149 (2017.01)
G06T 7/155 (2017.01)
G06T 7/136 (2017.01)
A61B 5/103 (2006.01)

(52) U.S. Cl.
CPC ............ *G06T 7/11* (2017.01); *G06T 7/136* (2017.01); *G06T 7/149* (2017.01); *G06T 7/155* (2017.01); *A61B 5/1034* (2013.01); *G06T 2207/10024* (2013.01); *G06T 2207/20041* (2013.01); *G06T 2207/20116* (2013.01); *G06T 2207/30088* (2013.01); *G06T 2207/30096* (2013.01)

(56) References Cited

U.S. PATENT DOCUMENTS

| | | | | |
|---|---|---|---|---|
| 2010/0098306 | A1* | 4/2010 | Madabhushi | G06K 9/0014 382/128 |
| 2017/0039704 | A1* | 2/2017 | Kasmi | G06T 7/0012 |
| 2017/0169276 | A1* | 6/2017 | Agaian | G16H 50/30 |
| 2018/0103892 | A1* | 4/2018 | Kaur | A61B 5/444 |

OTHER PUBLICATIONS

Caselles, Vicent et al., A geometric model for active contours in image processing, Numedsche Mathematik 9 Springer-Verlag 1993k pp. 1-31, Mathematics Subject Classification (1991).
Caselles, Vicent et al., Geodesic Active Contours, International Journal of Computer Vision 22(1), Copyright 1997 Kluwer Academic Publishers. Manufactured in The Netherlands, pp. 61-79.
Celebi, M. Emre et al., Lesion Border Detection in Dermoscopy Images Using Ensembles of Thresholding Methods, Skin Research and Technology 2013; 19: © 2012 John Wiley & Sons A/S, Printed in Singapore, doi: 10.1111/i.1600-0846.2012.00636.x, pp. e252-e258.
Chung, Do Hyun, Segmenting Skin Lesions with Partial-Differential-Equations-Based Image Processing Algorithms, IEEE Transactions on Medical Imaging, vol. 19, No. 7, Jul. 2000, pp. 763-767.
Dhawan, Atam P. et al., Segmentation of Images of Skin Lesions Using Color and Texture Information of Surface Pigmentation, Computerized Medical Imaging and Graphics. vol. 16, No. 3, 1992, pp. 163-177.
Ercal, F. et al., Detection of Skin Tumor Boundaries in Color Images, IEEE Transactions on Medical Imaging, vol. 12, No. 3, Sep. 1993, pp. 624-627.
Erkol, Bulent et al., Automatic lesion boundary detection in dermoscopy images using gradient vector flow snakes, Skin Research and Technology 2005; 11: pp. 17-26.
Garnavi, Rahil et al., Computer-Aided Diagnosis of Melanoma Using Border- and Wavelet-Based Texture Analysis, IEEE Transactions on Information Technology in Biomedicine, vol. 16, No. 6, Nov. 2012, pp. 1239-1252.
Han, Xiao et al., A Topology Preserving Level Set Method for Geometric Deformable Models, IEEE Transactions on Pattern Analysis and Machine Intelligence, vol. 25, No. 6, Jun. 2003, pp. 755-768.
Hand, Gregory A. et al., Unsupervised Color Image Segmentation—With application to skin tumor borders, IEEE Engineering in Medicine and Biology, 0739-51 75/96/$4.0001996, Jan./Feb. 1996, pp. 104-111.
Huang, Shaohui et al., Using GVF Snake to Segment Liver from CT Images, Proceedings of the 3rd IEEE-EMBS International Summer School and Symposium on Medical Devices and Biosensors MIT, Boston, USA, Sep. 4-6, 2006, pp. 145-148.
Iyatomi, Hitoshi et al., An improved Internet-based melanoma screening system with dermatologist-like tumor area extraction algorithm, Available online at www.sciencedirect.com, Computerized Medical Imaging and Graphics 32 (2008), pp. 566-579.
Kass, Michael et al., Schlumberger Palo Alto Research, Snakes: Active Contour Models, International Journal of Computer Vision, (1988) Copyright 1987 Kluwer Academic Publishers, Boston, Manufactured in The Netherlands, pp. 321-331.
Lee, Cheolha Pedro, Robust Image Segmentation using Active Contours: Level Set Approaches, Department of Electrical and Computer Engineering, Raleigh, 2005, pp. ii-x, pp. 1-135.
Malladi, Ravikanth et al., Shape Modeling with Front Propagation: A Level Set Approach, IEEE Transactions on Pattern Analysis and Machine Intelligence, vol. 17, No. 2, Feb. 1995, pp. 158-175.
Osher, Stanley et al., Fronts Propagating with Curvature Dependent Speed: Algorithms Based on Hamilton-Jacobi Formulations, Journal of Computational Physics, 79, (1988) pp. 12-49.
Osher, Stanley et al., Level Set Methods and Dynamic Implicit Surfaces, Los Angeles, California, web sites: http://graphics.stanford.edu/~fedkiw and http://www.math.ucla.edu/~sjo/, pp. 1-273.
Otsu, Nobuyuki, A Threshold Selection Method from Gray-Level Histograms, 2EEE Transactions on Systrems, Man, and Cybernetics, vol. SMC-9, No. 1, Jan. 1979, pp. 62-66.
Sethian, J.A., Level Set Methods and Fast Marching Methods, Evolving Interfaces in Computational Geometry, Fluid Mechanics, Computer Vision, and Materials Science, Dept. of Mathematics University of California Berkeley, Cambridge University Press, 1999downloaded from:http://math.berkeley.edu/sethian/level set. html., pp. xiii-xxii, pp. 3-13, pp. 359-378.
Wang, Hanzheng et al., Watershed segmentation of dermoscopy images using a watershed technique, Skin Research and Technology 2010; 16: pp. 378-384.
Wollina, Uwe et al., Digital dermoscopy in clinical practise: a three-centre analysis, Skin Research and Technology 2007; 13:Journal compilation & 2007 Blackwell Munksgaard doi: 10.1111/j.1600-0846.2007.00219., pp. 133-142.
Wong, Alexander, Automatic Skin Lesion Segmentation via Iterative Stochastic Region Merging, IEEE Transactions on Information Technology in Biomedicine, vol. 15, No. 6, Nov. 2011, pp. 929-936.
Xu, Chenyang et al., Snakes, Shapes, and Gradient Vector Flow, IEEE Transactions on Image Processing, vol. 7, No. 3, Mar. 1998, pp. 359-369.
Yeo, Si Yong, Implicit Active Contours for N-Dimensional Biomedical Image Segmentation, 2012 IEEE International Conference on Systems, Man, and Cybernetics Oct. 14-17, 2012, COEX, Seoul, Korea, pp. 2855-2860.
Yuksel, Emin et al., Accurate Segmentation of Dermoscopic Images by Image Thresholding Based on Type-2 Fuzzy Logic, IEEE Transactions on Fuzzy Systems, vol. 17, No. 4, Aug. 2009, pp. 976-982.
M. Emre Celebi et al. Border detection in dermoscopy images using statistical region merging. Skin Research and Technology. vol. 14. pp. 347-353. 2008.
R. Kasmi et al. "Biologically inspired skin lesion segmentation using a geodesic active contour technique". Skin Research and Technology. vol. 22. pp. 208-222. 2016.

\* cited by examiner

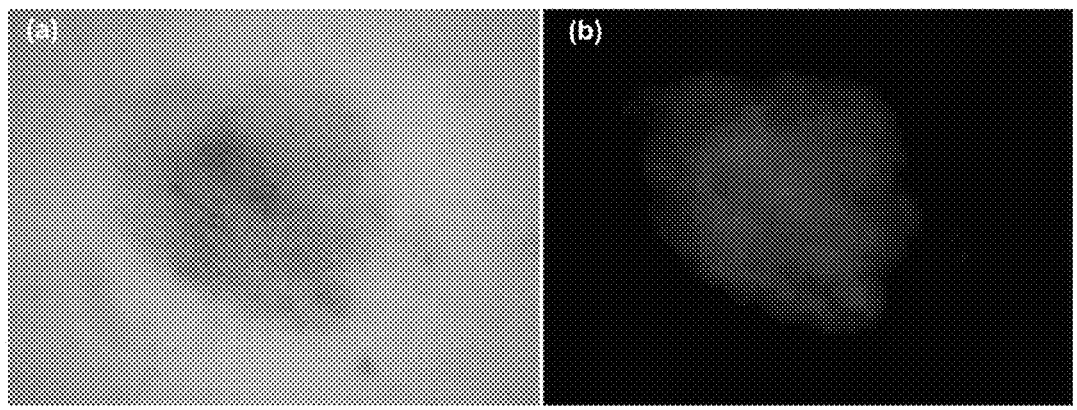
FIG. 3A                    FIG. 3B
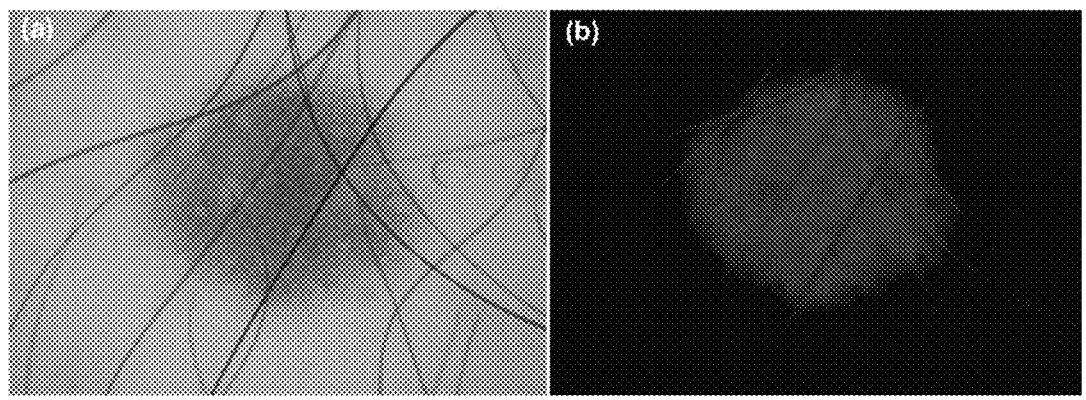
FIG. 4A                    FIG. 4B Algorithm 2; a = 40

Algorithm 1; a = 60

Algorithm 2; a = 90

Algorithm 1; a = 110

Algorithm 2; a = 110

Algorithm 1; a = 130

Algorithm 2; a = 130

DETECTION OF BORDERS OF BENIGN AND MALIGNANT LESIONS INCLUDING MELANOMA AND BASAL CELL CARCINOMA USING A GEODESIC ACTIVE CONTOUR (GAC) TECHNIQUE

CROSS REFERENCE TO RELATED APPLICATIONS

This U.S. Non-Provisional Patent Application claims priority to U.S. Provisional Patent Application No. 62/181,075, filed Jun. 17, 2015. The priority application is incorporated herein by reference in its entirety for all purposes.

BACKGROUND

Worldwide, malignant melanoma was responsible for an estimated 49,100 deaths in 2010, yet when detected at the earliest (in situ) stage, there is no change in life expectancy. Thus, early detection of malignant melanoma is critical. In private practices throughout the USA, patients are appearing in clinics with smaller, earlier lesions, before the classic features of melanoma have become fully apparent. In one study, 21% of melanomas in situ were smaller than 6 mm in greatest diameter.

SUMMARY

An embodiment of the present invention may comprise a lesion segmentation method performed on a computer system that automatically finds a border of a lesion shown in a digital image based on a gray scale version (IG) of the image and on a Red-Green-Blue (RGB) component color version (Irgb) of the image, the method comprising: smoothing the grayscale image by convolving the gray scale image with a first spatial filter to generate a smoothed gray scale image; extracting each pixel value of a blue component plane of the RGB color image from each corresponding pixel value of a red component plane of the RGB color image to generate an extracted image; extracting each pixel value of the smoothed gray scale image from each corresponding pixel value of the extracted image to generate a new image; smoothing the new image by convolving the new image with a second spatial filter to generate a smoothed new image; binarizing the smoothed new image to generate a black and white image; and constructing the border of the lesion as a contour of a pixel width edge between black portions and white portions of the black and white image.

An embodiment of the present invention may further comprise a lesion segmentation computer system implementing the processes of the above described lesion segmentation method. Further, in describing the lesion segmentation computer system one or more individual processes described above for the lesion segmentation method may be broken down and represented as a subsystem of the overall lesion segmentation computer system. A subsystem of the lesion segmentation computer system may be assigned, in whole or in part, to a particular hardware implemented system, such as a dedicated Application Specific Integrated Circuit (ASIC) or Field Programmable Gate Array (FPGA). One or more subsystems, in whole or in part, may alternatively be implemented as software or firmware instructions defining the operation of a computer system with specific regard to the one or more subsystems implemented as software or firmware instructions. The software or firmware instructions may cause the Central Processing Unit, memory, and/or other systems of a computer system to operate in particular accordance with the particular one or more subsystems designated features.

In certain embodiments, a system for implementing the processes of the above described lesion segmentation method may include a processor and a memory comprising one or more computer readable media having computer-executable instructions embodied thereon, wherein, when executed by the processor, the computer-executable instructions cause the processor to perform the above described lesion segmentation method.

In other embodiments, one or more computer-readable media have computer-executable instructions embodied thereon for lesion segmentation as described above, wherein, when executed by a processor, the computer-executable instructions cause the processor to perform the above described lesion segmentation method.

Additionally various embodiments of the present invention may further provide alternate choices for segmentation to provide alternate borders, proving advantageous for computing optimal segmentation choices for the wide variety of lesions encountered in practice. A best-fit lesion border may be selected from the alternate borders. In some embodiments, the best-fit lesion border may be selected automatically.

BRIEF DESCRIPTION OF THE DRAWINGS

The patent or application file contains one or more drawings executed in color and/or one or more photographs. Copies of this patent or patent application publication with color drawings and/or photographs will be provided by the Patent Office upon request and payment of the necessary fee.

FIGS. 3A-3B: Photographs showing an original image without hair (FIG. 3A) and the corresponding new image $I_{newsth}$ (FIG. 3B).

FIGS. 4A-4B: Photographs showing an original image with hair (FIG. 4A) and the corresponding new image $I_{newsth}$ (FIG. 4B).

FIGS. 19A-19K: Examples of border results for Algorithms 1 and 2, using different values for parameter a:

FIG. 19A—Algorithm 1, a=16;
FIG. 19B—Algorithm 1, a=40;
FIG. 19C—Algorithm 2, a=40;
FIG. 19D—Algorithm 1, a=60;
FIG. 19E—Algorithm 2, a=60;
FIG. 19F—Algorithm 1, a=90;
FIG. 19G—Algorithm 2, a=90;
FIG. 19H—Algorithm 1, a=110;
FIG. 19I—Algorithm 2, a=110;
FIG. 19J—Algorithm 1, a=130; and
FIG. 19K—Algorithm 2, a=130.

DETAILED DESCRIPTION

Though early malignant melanoma detection is lifesaving, it is more difficult to diagnose a lesion in the early stages of the disease, creating an opportunity for computer-assisted diagnosis (CAD). Significant improvements in skin imaging technology and image processing can allow researchers to use these techniques to improve CAD for earlier melanoma detection.

Segmentation of skin lesions is an important step in CAD of skin cancer. Segmentation determines a border or contour that separates the lesion from the surrounding skin, and the extraction of clinical dermoscopy features, such as atypical pigment network and color, depend on the accuracy of segmentation. The contour is most commonly one picture element (pixel) wide, and is closed, completely enclosing a single undivided part of the image. The conventional goal of segmentation is to include, approximately, the skin lesion, specifically as much of the skin lesion as possible to the exclusion of surrounding skin. Success of segmentation is traditionally measured by the two types of error involved: 1) the amount of the surrounding skin included within the border; and 2) the amount of the lesion not included within the border.

Figure 1:
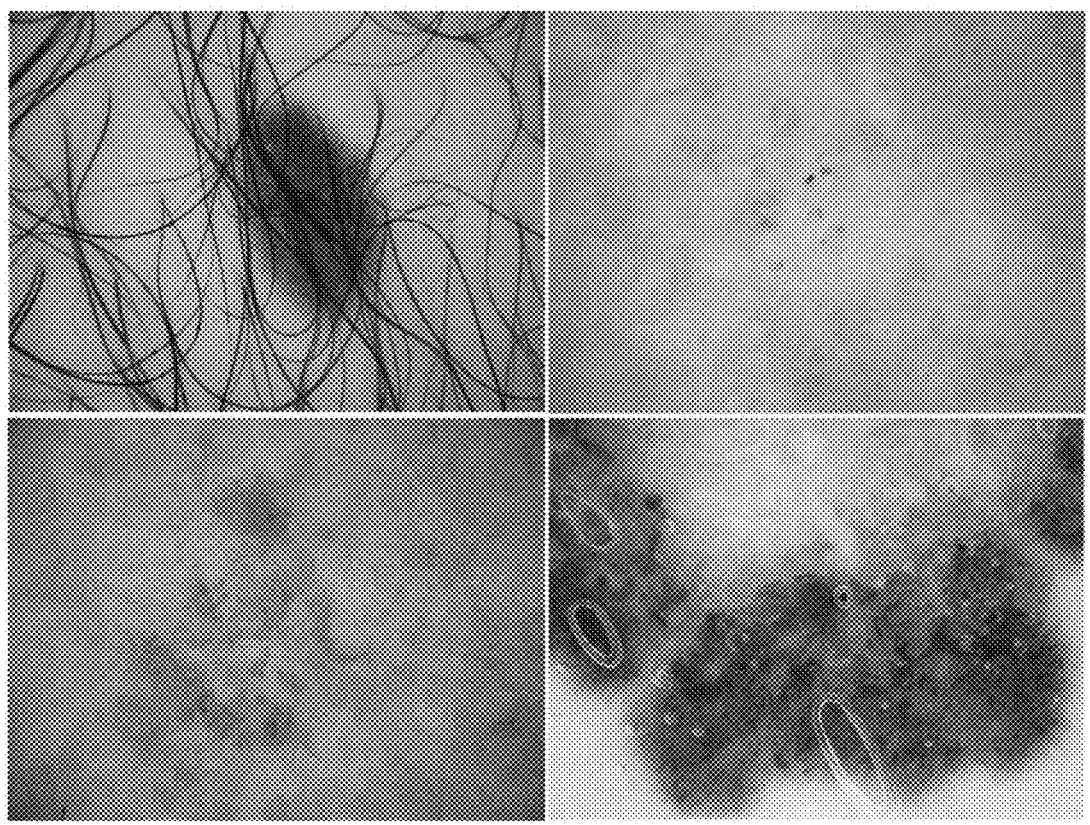
FIG. 1: Photographs of a variety of lesions that make dermoscopy image segmentation difficult.

Segmentation can be one of the most difficult problems in lesion image processing due to the variation in lesion shapes, sizes, and colors, as well as artifacts (e.g., gel-interface bubbles, ruler markings, and hair) and the variety of human skin (FIG. 1). Because segmentation can be a fundamental step in this area, automated approaches can provide particular value for dermoscopy imaging Automated approaches can face particular challenges when the surrounding skin regions are not homogeneous. It would be beneficial to develop an automated segmentation method capable of finding accurate lesion contours despite the presence of artifacts and variations in illumination, structure, color and weak boundary strength that characterize early lesions and atypical nevi with gradual separation between lesion and surrounding skin.

Described herein is a novel approach for automatic segmentation of dermoscopy images of skin lesions. The approach utilizes an algorithm that generates better skin lesion segmentation results than previously obtainable with active contours. As described herein, geodesic active contour (GAC) initialization is successfully automated to lie near the actual lesion contour. In addition, a new image plane is found by transforming the original RGB image to a smoothed image that allows the GAC to move without sticking on the minimum local energy.

An automated approach that utilizes active contour models ("snakes") can provide lesion segmentation when the snakes lock onto nearby edges as the snakes are able to localize the edges. However, noise in the dermoscopy images (e.g., hairs, rulers, and ulcers) often have sharp edges and the snake contour may stick on these edges rather than the lesion edge. The gradient vector field contour technique (GVF) snake model can provide a larger capture range and better ability to find concavities than the traditional snake model, but the GVF snake model remains susceptible to sticking on noisy artifacts. Some embodiments of the lesion segmentation method described herein automatically finds the skin lesion border while avoiding errors commonly encountered during segmentation, including, for example: 1) the resulting border being too small, usually caused by finding a single region in the skin lesion and not the entire lesion; and 2) the border is erroneous due to border sticking to noise such as hair, bubbles, camera flash, skin shading, or dark rings around the image caused by the camera.

As used herein, the term 'dermoscopy' refers to a body imaging technique that involves viewing skin lesions with 8× or more magnification. The technique involves limiting surface reflectance through the use of, for example, a fluid, gel, mineral oil, or alcohol between the skin and a glass plate, or by using cross polarized light for illumination. The term 'dermoscopy image' refers to a photograph of a skin lesion generated using a dermoscopy technique. In certain embodiments, the dermoscopy image is a digital image. Dermoscopy images can be acquired using any method known in the art, including but not limited to using a specialized dermoscopy imaging platform and inexpensive digital cameras with a dermoscopy-specific attachment or lens.

Theoretical Basis
Curve Evolution Theory and Level Sets

Classified as geometric deformable models, and based on the theory of front evolution, curves can be implemented using the level set numerical method described by, for example, X. Han, C. Xu, and J. L: Prince, IEEE Trans. Patt. Analysis Mach. Intell., vol. 25, pp. 755-768 (2003), J. A. Sethian, Level Set Methods and Fast Marching Methods, 2nd ed. Cambridge, UK: Cambridge Univ. Press (1999), and C. P. Lee, Robust image segmentation using active contours: level set approaches," Ph.D. thesis, Dept. Elec. Comput.

Engr., N. Carolina State U., Raleigh N.C. (2005), all of which are incorporated by reference in their entirety.

Let $\vec{C}(p)=\{(x(p),y(p)),p\in[0,1]\}$ be the initial contour.

The partial differential equation of the curve defines a velocity $\vec{V}$ on every point p in the curve at time t as:

$$\frac{\partial C(p)}{\partial t} = \vec{V}(p, t). \tag{1}$$

The curve evolution is the normal component of the velocity, while the tangential component does not affect the shape of the curve (C. P. Lee Thesis (2005)).

The evolution equation can be written as:

$$\frac{\partial C(p, t)}{\partial t} = F(C(p, t))\vec{n}, \tag{2}$$

where $F(C(p,t))$ is the scalar function of the curvature k of the contour, and $\vec{n}$ is the unit inward vector normal to the contour $C(p,t)$.

Geodesic Active Contour

The Geodesic Active Contour (GAC) is based on curve evolution theory and describes where the contour is evolving in the normal direction, multiplying the contour velocity by an additional term, called the stopping function, that is a monotonically decreasing function of the gradient magnitude of the image, as in the equation:

$$\frac{\partial C(t)}{\partial t} = \left(g(I)k - <\nabla g(I)\vec{N}>\right)\vec{N} \tag{3}$$

$$g(I) = \frac{1}{1 + (\nabla I)^2}, \tag{4}$$

where $\nabla I$ is the gradient of the gray scale of the image; g is a decreasing function; k is curvature; and $\vec{N}$ is a unit vector in the normal direction.

Level Sets

Level set theory is a model to implement active contours. In this model, the contour is represented implicitly on the two dimensional Lipschitz-continuous function called the level set $\emptyset(x,y)$ defined on the image. The contour on the level set function is the zero level:

$$C=\{(x,y)|\emptyset(x,y)=0\}, \text{ where} \tag{5}$$

$\emptyset$ is the level set function, and $$\emptyset(x, y) = \begin{cases} 0: & (x, y) \text{ is inside } C \\ = 0: & (x, y) \in C \\ > 0 & (x, y) \text{ is outside } C \end{cases} \tag{6}$$

Figure 2:
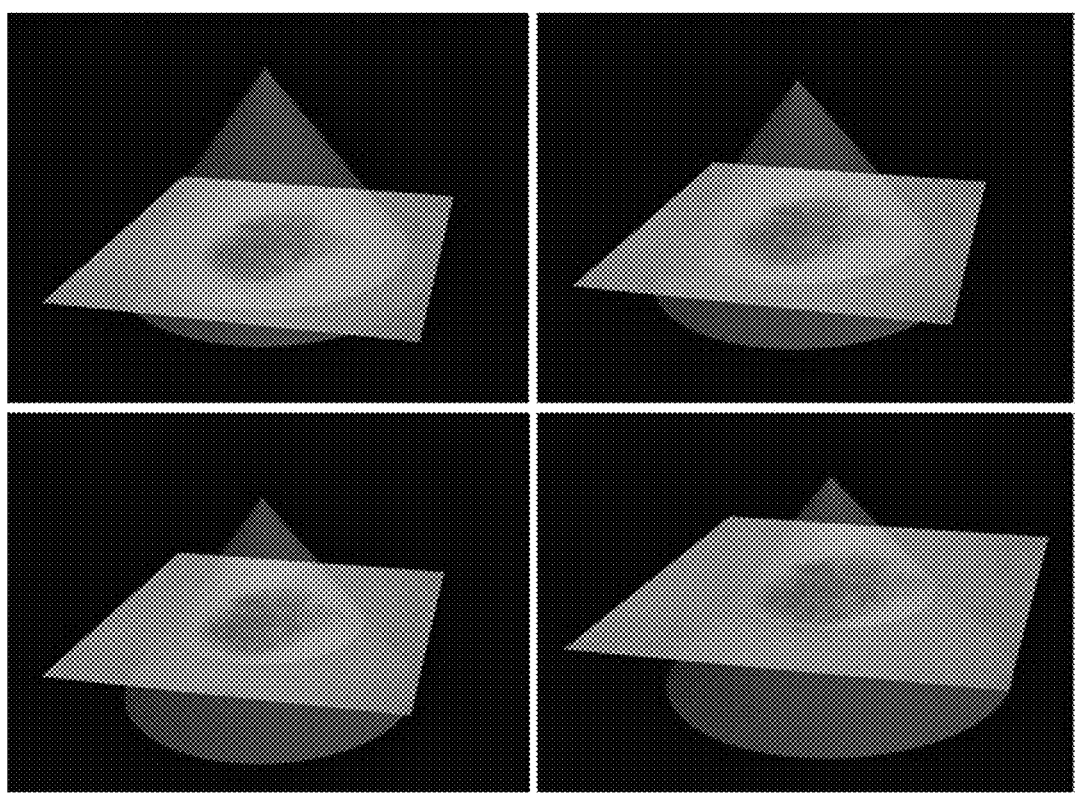
FIG. 2: Diagrams showing evolution of the level set contour toward the lesion contour, where the intersection of Ø and the image correspond to the zero level.

FIG. 2 demonstrates an example of the evolution of the level set contour toward the lesion contour, where the intersection of $\emptyset$ and the image correspond to the zero level.

Implementation of GAC

Methods of certain embodiments are described below. Image 'planes' are described in matrix notation. For example, the notation R is used for the red plane and the notation IG is used for the gray scale image, further described below. The alternate matrix notation R(i,j) and IG(i,j) is equivalent.

Level Set Implementation

The implementation of the GAC algorithm is based on level set methods. The contour evolution using $\emptyset(x,y)$ can be defined as:

$$\frac{\partial \emptyset(x, y)}{\partial t} = |\nabla \emptyset(x, y)|(v + \varepsilon k), \tag{7}$$

where v denotes a constant speed term to push or pull the contour, and k is the curvature of the level set function. The role of the curvature term is to control the regularity of the contours, and ε controls the balance between the regularity and robustness of the contour evolution.

The resulting level set update equation can be written as:

$$\emptyset(x,y,t_{m+1})=\emptyset(x,y,t_m)+\Delta t\Delta\emptyset(x,y,t_m), \tag{8}$$

where $\Delta t=t_{m+1}-t_m$ time step.

Image Smoothing and Transformation

The presence of edges in skin comprises the main drawback of using active contour methods in this domain. To overcome GAC sticking at these minimum energy edges, an image transformation method was developed that can facilitate lesion enhancement, reduction in background intensity, and removal of most hairs and other edge noise.

The grayscale image IG is the luminance plane, which in certain embodiments, can be obtained by the luminance formula IG=0.2989*R+0.5870*G+0.1140*B, where R, G, and B represent the red, green, and blue color planes, respectively. IG is smoothed by convolving with a (4×4) spatial filter H1:

$$H1 = \frac{1}{a} \times \begin{bmatrix} 1 & 1 & 1 & 1 \\ 1 & 1 & 1 & 1 \\ 1 & 1 & 1 & 1 \\ 1 & 1 & 1 & 1 \end{bmatrix} \tag{9}$$

$$IGsth = IG * H1, \tag{10}$$

where IG is the grayscale image; * represents a convolution operation, and × represents multiplication of a matrix by a scalar.

Value a can be any value from about 40 to about 130 (see FIG. 19, showing borders using different a values). In certain embodiments, value a is 90.

A common color plane used for automatically identifying contours of skin lesions is the blue plane, specifically the blue (B) component of the digital RGB image. However, it was found that the difference between the red and blue planes better approximates the biological image. In certain embodiments, the blue plane and the smoothed grayscale image $IG_{sth}$ are successively extracted from the red plane. Extraction is used rather than subtraction in order to create a border which is simultaneously binary, sufficiently large, and which greatly reduces noise from, for example, hair, ruler marks, and other objects. Extraction denotes subtraction of planes with negative values set to zero. For the entire image, formally: $\forall\{i,y\}\cup\Omega$ $$Irb(i, j) = \begin{cases} 0 & \text{if} \quad (R(i, j) - B(i, j)) < 0 \\ (R(i, j) - B(i, j)) & \text{Otherwise} \end{cases} \tag{11}$$

-continued $$Irgs = Irb - IG_{sth} \quad (12)$$

$$I_{new}(i, j) = \begin{cases} 0 & \text{if} \quad (Irb(i, j) - IG_{sth}(i, j)) < 0 \\ Irb(i, j) - IG_{sth}(i, j) & \text{Otherwise} \end{cases} \quad (13)$$

Finally, $I_{newsth}$ is created from $I_{new}$ by convolving with a 10×10 spatial filter H2.

$$H2 = \frac{1}{b} \times \begin{pmatrix} 1 & \cdots & 1 \\ \vdots & \ddots & \vdots \\ 1 & \cdots & 1 \end{pmatrix} \quad (14)$$

$$I_{newsth} = IG * H2; \quad (15)$$

where * denotes the convolution operation, and x denotes multiplication of a matrix by a scalar.

FIGS. 3-4 show examples of the new plane $I_{newsth}$, and show that the transformed $I_{newsth}$ enhances the lesion and removes noise and most hair from the original image. Value b can be any value from about 100 to about 2500 (see FIG. 19, showing borders using different b values). In certain embodiments, value b is 100.

Contour Initialization

One objective of contour initialization is to automatically find an initial contour. The new plane $I_{initial}$ (equation 17) is binarized by a threshold T=(OtsuThreshold−10). Some embodiments can use the most basic binary transformation, that being setting the threshold/breakpoint at half of the total (half of 255 for the depth discussed in the example embodiments discussed herein) and then adapting the threshold up or down from that halfway point. Other methods of binarizing an image may be used to create a black and white image from a grayscale or other image with a depth of greater than two. A successful binarization can be characterized by providing adaptability, that is the threshold chosen is capable of choosing a darker (i.e. lower) threshold for a darker lesion, and a lighter (i.e., higher) threshold for a lighter lesion. The Otsu threshold (see, e.g., B. Erkol et al., Skin Res. Technol., vol. 11, no. 1, pp. 17-26 (2005)) finds a threshold that separates the two classes of pixels so that their combined spread (intra-class variance) is minimal, or equivalent (because the sum of pairwise squared distances is constant). Experimentation has confirmed that Otsu's method generally finds too small a lesion area. That is, the resulting border typically does not enclose the entire lesion. It can be advantageous to modify the basic Otsu threshold to account for this. Further analysis confirmed that the Otsu threshold results improve when reduced by 10 on a scale of 255. The binary image found is extended by a structuring element using mathematical morphology (the extended image still being a binary image). An adaptive disk structuring element with optimized radius r is computed by equations 19 and 20. Arbitrary contour initialization usually induces boundary sticking at undesirable edges on the image due to the large intensity variations which often exist in biomedical images, and increases computation when the initial contour is too far from the actual contour. Yet a wide initial contour can facilitate avoidance of erroneously small final contours. The GAC method deforms and evolves the initial contour until it is stuck on the final lesion border. Automatic contour initialization is introduced to create a contour well outside the lesion, yet not too far outside, therefore potentially mitigating these problems.

The new image $I_{newsth}$ is again smoothed, using a 30×30 median filter. The resulting image $I_{newsth30}$ is then convolved with a 40×40 spatial filter H3:

$$H3 = \frac{1}{c} \times \begin{pmatrix} 1 & \cdots & 1 \\ \vdots & \ddots & \vdots \\ 1 & \cdots & 1 \end{pmatrix} \quad (16)$$

$$I_{initial} = I_{newsth30} * H3 \quad (17)$$

where * denotes the convolution operation, and x denotes multiplication of a matrix by a scalar.

Value c can be any value from about 1000 to about 2200. In a particular embodiment, value c is 1600.

The Otsu threshold is computed from $I_{initial}$. The basic Otsu threshold is modified in some embodiments, as explained below. The lesion is expanded by reducing the Otsu threshold by 10, on a scale of 255, with the Otsu threshold optimized for dermoscopy images. In the case where the new threshold is under zero, it was set to eps=2.2204e−16. $I_{initial}$ (equation 17) is therefore binarized (binary image created) by T=(OtsuThreshold-10), meaning if a given pixel in the $I_{initial}$ image is greater than T, the pixel is forced to 0, and forced to 1 otherwise, resulting in a black and white image (mask). S=area of the lesion=white part of the segmentation (number of 1s in the mask) and background is the black part of the segmentation. The initial contour is the boundary between 0 and 1. If the meaning of the 1 and 0 are reversed such that the 0s represent white and the 1's represent black, the operation of an embodiment would be substantially identical with a simple reversal of the operations regarding the consideration of what is black and what is white.

$$\text{threshold} = \begin{cases} \text{Otsu Threshold} - 10 \\ eps \text{ if (Otsu Threshold} - 10) < 0 \end{cases} \quad (18)$$

Figure 5:
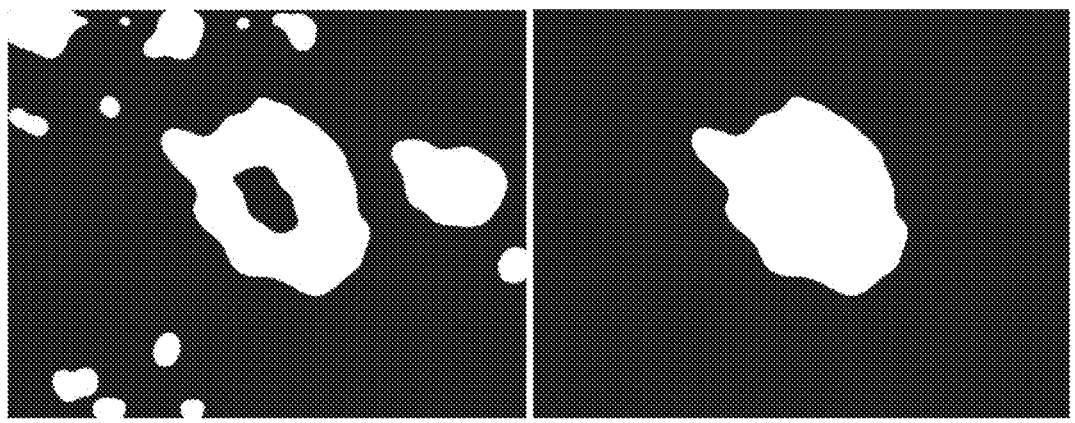
FIG. 5: Images showing lesion contour object selection after binarization (left; object closest to the center of the image is selected), and filling of the selected object (right).

Extraneous regions may appear after binarization (see FIG. 5). The lesion contour is chosen as the closest object to the center of the image, and then the object is filled. Filling of the object comprises finding a hole in the object. A hole=an area of 0s (i.e., black) surrounded on all sides by 1s (i.e., white). To fill the hole, all 0s enclosed within the object are forced to a value of 1.

The initial contour is the contour of the dilated object created using mathematical morphology. An adaptive disk structuring element with optimized radius r is computed as:

$$S2 = K \times S \quad (19)$$

$$r = \sqrt{S2} \quad (20)$$

K was obtained by comparing the average area obtained for 100 images for three dermatologists compared to the average obtained by K values of 0.002 and 0.003. A K value of 0.00275 was obtained by interpolation, to yield an average area obtained for the new method equal to the average area obtained by the three dermatologists. In some embodiments, K is set to 0.00275. After this operation, the initial contour is obtained, still implemented as a binary image represented as a lesion (represented, e.g., by 1s, which may be white in the black and white figures) and background (represented, e.g., by 0s, which may be black in the black and white figures). In particular embodiments, the initial contour is the outer-most pixels at the edge of the white image area.

The level set function is calculated:

$$\emptyset = \text{DistFct}(\text{Msk}) - \text{DistFct}(1-\text{Msk}), \quad (21)$$

where DistFct is a Euclidean distance transform, and Msk is the lesion binary mask of the lesion and 1-Msk is the inverted mask representing non-lesion. The Euclidean distance transform in one implementation shown here using MatLab computes the Euclidean distance for each background point in the mask (Msk (0s)) to the closest boundary point (point at the edge) between 0s and 1s (edge of Msk 1s)), as shown, for example, in Table 1. The distance-transformed image converts the binary image to a gray scale image.

TABLE 1

Representative binary image and associated distance transformation results using the MatLab function bwdist( ).

| | | | | | | | |
|---|---|---|---|---|---|---|---|
| A = | 0 | 0 | 0 | 0 | 0 | 0 | 0 |
| | 0 | 0 | 0 | 0 | 0 | 0 | 0 |
| | 0 | 0 | 1 | 1 | 1 | 0 | 0 |
| | 0 | 0 | 1 | 1 | 1 | 0 | 0 |
| | 0 | 0 | 1 | 1 | 1 | 0 | 0 |
| | 0 | 0 | 0 | 0 | 0 | 0 | 0 |
| | 0 | 0 | 0 | 0 | 0 | 0 | 0 |
| bwdist(A) = | 2.8284 | 2.2361 | 2.0000 | 2.0000 | 2.0000 | 2.2361 | 2.8284 |
| | 2.2361 | 1.4142 | 1.0000 | 1.0000 | 1.0000 | 1.4142 | 2.2361 |
| | 2.0000 | 1.0000 | 0 | 0 | 0 | 1.0000 | 2.0000 |
| | 2.0000 | 1.0000 | 0 | 0 | 0 | 1.0000 | 2.0000 |
| | 2.0000 | 1.0000 | 0 | 0 | 0 | 1.0000 | 2.0000 |
| | 2.2361 | 1.4142 | 1.0000 | 1.0000 | 1.0000 | 1.4142 | 2.2361 |
| | 2.8284 | 2.2361 | 2.0000 | 2.0000 | 2.0000 | 2.2361 | 2.8284 |
| 1-A = | 1 | 1 | 1 | 1 | 1 | 1 | 1 |
| | 1 | 1 | 1 | 1 | 1 | 1 | 1 |
| | 1 | 1 | 0 | 0 | 0 | 1 | 1 |
| | 1 | 1 | 0 | 0 | 0 | 1 | 1 |
| | 1 | 1 | 0 | 0 | 0 | 1 | 1 |
| | 1 | 1 | 1 | 1 | 1 | 1 | 1 |
| | 1 | 1 | 1 | 1 | 1 | 1 | 1 |
| bwdist(1-A) = | 0 | 0 | 0 | 0 | 0 | 0 | 0 |
| | 0 | 0 | 0 | 0 | 0 | 0 | 0 |
| | 0 | 0 | 1 | 1 | 1 | 0 | 0 |
| | 0 | 0 | 1 | 2 | 1 | 0 | 0 |
| | 0 | 0 | 1 | 1 | 1 | 0 | 0 |
| | 0 | 0 | 0 | 0 | 0 | 0 | 0 |
| | 0 | 0 | 0 | 0 | 0 | 0 | 0 |
| bwdist(A) − bwdist(1-A) = | 2.8284 | 2.2361 | 2.0000 | 2.0000 | 2.0000 | 2.2361 | 2.8284 |
| | 2.2361 | 1.4142 | 1.0000 | 1.0000 | 1.0000 | 1.4142 | 2.2361 |
| | 2.0000 | 1.0000 | −1.0000 | −1.0000 | −1.0000 | 1.0000 | 2.0000 |
| | 2.0000 | 1.0000 | −1.0000 | −2.0000 | −1.0000 | 1.0000 | 2.0000 |
| | 2.0000 | 1.0000 | −1.0000 | −1.0000 | −1.0000 | 1.0000 | 2.0000 |
| | 2.2361 | 1.4142 | 1.0000 | 1.0000 | 1.0000 | 1.4142 | 2.2361 |
| | 2.8284 | 2.2361 | 2.0000 | 2.0000 | 2.0000 | 2.2361 | 2.8284 |

Level Set Implementation

Figures 6A, 6B:
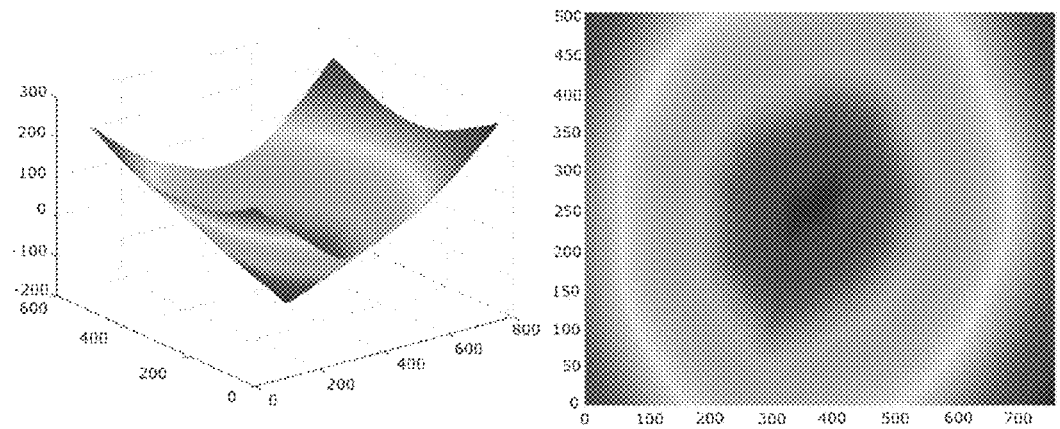
FIGS. 6A-6B: Images showing level set function Ø 3D (FIG. 6A) and Ø 2D (FIG. 6B).

The level set is computed by equation (21); the result is a grayscale image. In the middle, pixels are negative (under zero). Moving from the middle of the grayscale image toward the outer portion, the value of pixels passes through the level where pixels have a zero value and become positive, shown in 3D in FIG. 6A, where the contour consists of three levels: negative levels, zero level and positive levels. Thus a level set is a grayscale image with positive levels (pixels value>0) and negative levels (pixels value<0), separated by zero level (pixels value=0). The GAC moves the initial contour computed from $I_{initial}$ (equation 17) until it is stopped by a high gradient on lesion edges.

GAC Contour Update Implementation Using Level Sets $$\emptyset_t = gk + \langle \nabla g, \nabla \emptyset \rangle$$

$\langle \nabla g, \nabla \emptyset \rangle$: Inner product $\nabla$: Gradient $$g = \frac{1}{1 + (\nabla \text{ Image})^2}$$

$$k = \text{Quotient}\left(\frac{\nabla \emptyset}{|\nabla \emptyset|}\right) = \frac{\emptyset_{xx}\emptyset_y^2 - 2\emptyset_{xy}\emptyset_x\emptyset_y + \emptyset_{yy}\emptyset_x^2}{\emptyset_x^2 + \emptyset_y^2}$$

$\emptyset_{xy}$: Second order partial derivative of $\emptyset$ with respect to x and y $\emptyset_x$: First order partial derivative of $\emptyset$ with respect to $$x = \frac{\partial \emptyset}{\partial x}$$

$\emptyset_y$: First order partial derivative of $\emptyset$ with respect to $$x = \frac{\partial \emptyset}{\partial y}$$

The resulting level set update equation can be written as $$\emptyset(x,y,t+1) = \emptyset(x,y,t) + \Delta t \Delta \emptyset(x,y,t),$$

where Δt is a constant equal to 0.9. In some embodiments, the number of iterations before re-initializing can be 3-7. In one embodiment, the number of iterations before re-initializing can be 5. The level set update equation is given first using gradient notation, defined in terms of partial derivatives, i.e. giving the derivatives the function Ø with respect to both x and y. This is simplified immediately above, which gives the update equation in terms of the time increment Δt and the function Ø increment ΔØ. The implementation given above follows Lee, 2005 (C. P. Lee, "Robust image segmentation using active contours: level set approaches," Ph.D. thesis, Dept. Elec. Comput. Engr., N. Carolina State U., Raleigh N.C., 2005, which is incorporated herein by reference in its entirety)

Parallel Paths for Alternate Borders

For images where segmentation errors exceed 30% (e.g., as in FIG. 15), a deterministic solution may not be desirable because 'tuning' or optimization for one type of image can lead to a larger error for another type of image. To overcome this limit, 12 additional image transformations were developed (Algorithms 2-13 below) that take into consideration the complexity and color variety in these lesions. With parallel border path generation for each lesion, any number of total border options can be generated, and the best border solution can be chosen.

Figure 17:
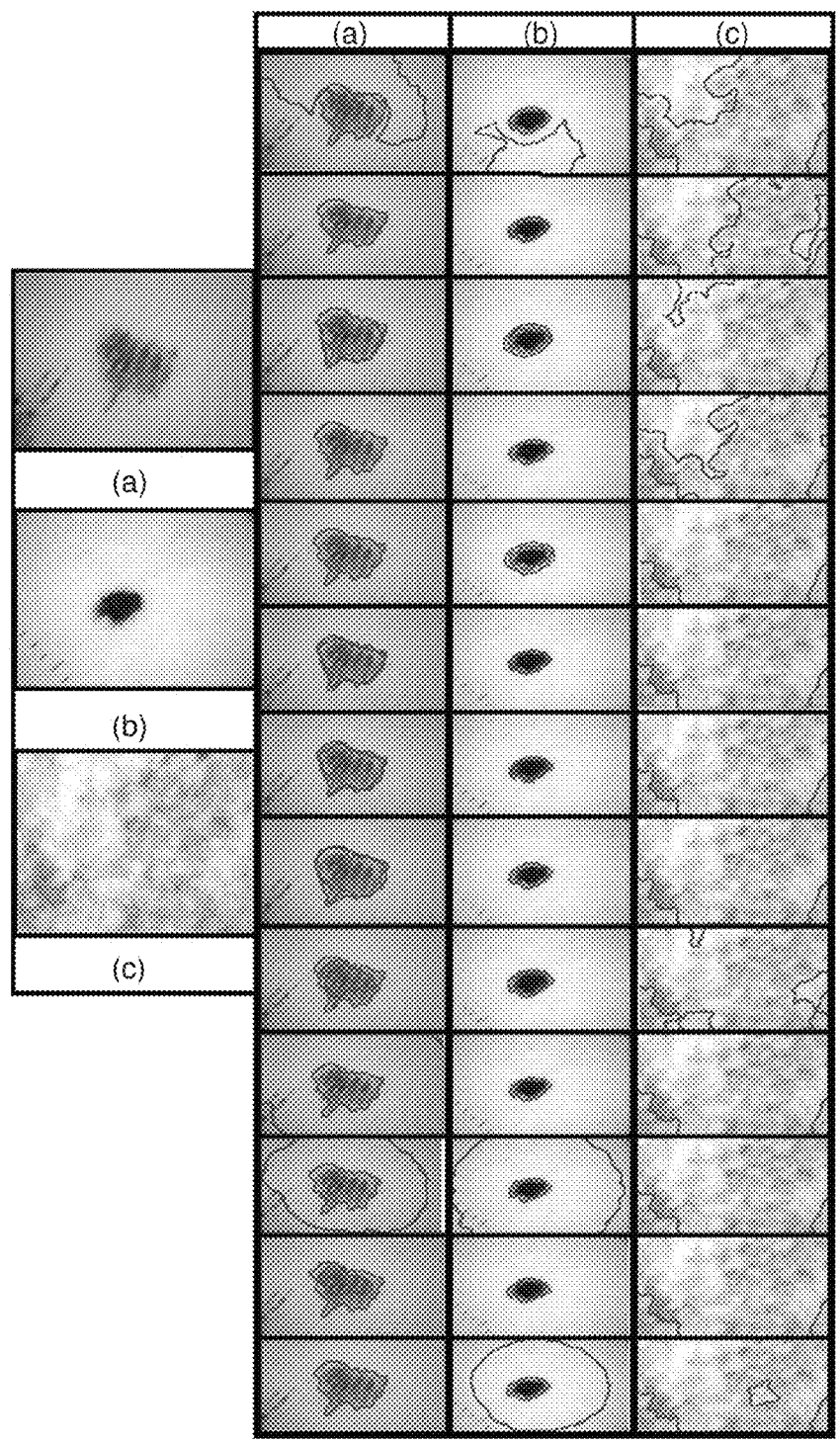
FIG. 17: Photographs showing three difficult lesions (lesions marked (a)-(c)) and the 13 borders (shown in blue) obtained from the primary GAC algorithm and the 12 options (Algorithms 1-13, from top to bottom).

The following 12 algorithms are transformations of the image that each generate additional borders for each image (FIG. 17). Algorithm 1 is the default algorithm presented above (equations 9-21). In the following equations, the isolated characters 'R' 'G' and 'B' refer to the red, green and blue planes, respectively.

Algorithms 2-13 replace equations 9 to 15 of the steps above, which comprise Algorithm 1. After these replacements, subsequent steps for algorithms 2-13, beginning with equation 16, and including post-processing steps detailed below for removal of peninsulas and inlets, remain unchanged.

Algorithm 2: The gray scale image IG is convolved with spatial filter H1 (equation 9).

$$IG2 = \begin{cases} 255 \text{ if } 5 \times IGsth > 255 \\ 5 \times IGsth \text{ otherwise} \end{cases} \quad (22)$$

$$I_{plan2} = (255 - IG2) + \frac{1}{3} \times IG2 \quad (23)$$

$I_{plan2}$ is filtered by Median filter using window size of [10,10].

Algorithm 3: The gray scale image IG is convolved with spatial filter H4:

$$H4 = \frac{1}{45} \times \begin{bmatrix} 1 & 1 & 1 & 1 \\ 1 & 1 & 1 & 1 \\ 1 & 1 & 1 & 1 \\ 1 & 1 & 1 & 1 \end{bmatrix} \quad (24)$$

$$IG3 = IG * H4 \quad (25)$$

$$IG31(i, j) = \begin{cases} 0 \text{ if } (R(i, j) - B(i, j)) < 0 \\ (R(i, j) - B(i, j)) \text{ Otherwise} \end{cases} \quad (26)$$

-continued $$IG32(i, j) = \begin{cases} 0 \text{ if } (IG31(i, j) - IG3(i, j)) < 0 \\ (IG31(i, j) - IG3(i, j)) \text{ Otherwise} \end{cases} \quad (27)$$

$$I_{plan3} = IG32 \quad (28)$$

$I_{plan3}$ is filtered by Median filter using window size of [10,10].

Algorithm 4:

$$I_{plan4}(i, j) = \begin{cases} 0 \text{ if } 50*(255 - B(i, j)) > 70 \\ 50*(255 - B(i, j)) \text{ if } 50*(255 - B(i, j)) > 70 \end{cases} \quad (29)$$

$I_{plan4}$ is filtered by Median filter using window size of [10,10]

Algorithm 5:

$$IG5 = 255 - R + G \quad (30)$$

$$IG5(i, j) = \begin{cases} 255 \text{ if } (255 - R(i, j)) + G(i, j) > 255 \\ 255 - R(i, j) + G(i, j) \text{ Otherwise} \end{cases} \quad (31)$$

$$I_{plan5}(i, j) = \begin{cases} 255 \text{ if } (255 - IG5(i, j))^2 > 255 \\ (255 - IG5(i, j))^2 \text{ Otherwise} \end{cases} \quad (32)$$

$I_{plan5}$ is filtered by Median filter using window size of [10,10].

Algorithm 6: First, the grayscale image IG is convolved with spatial filter H1 (equation 9). Then the blue plane is extracted from the resulting plane IG6.

$$IG6 = IG * H1 \quad (33)$$

$$I_{plan6}(i, j) = \begin{cases} 0 \text{ if } ((255 - IG6(i, j)) - B) < 0 \\ ((255 - IG6(i, j)) - B) \text{ Otherwise} \end{cases} \quad (34)$$

Algorithm 7: The grayscale image IG is convolved with [4,4] spatial filter H5. Then the blue plane is extracted from the resultant image IG7:

$$H5 = \frac{1}{40} \times \begin{bmatrix} 1 & 1 & 1 & 1 \\ 1 & 1 & 1 & 1 \\ 1 & 1 & 1 & 1 \\ 1 & 1 & 1 & 1 \end{bmatrix} \quad (35)$$

$$IG7 = IG * H5 \quad (36)$$

$$I_{plan7}(i, j) = \begin{cases} 0 \text{ if } ((255 - IG7(i, j)) - B) < 0 \\ ((255 - IG7(i, j)) - B) \text{ Otherwise} \end{cases} \quad (37)$$

Algorithm 8:

$$I81(i, j) = \begin{cases} 0 \text{ if } (B(i, j) - 0.65 \times R(i, j)) < 0 \\ (B(i, j) - 0.65 \times R(i, j)) \text{ Otherwise} \end{cases} \quad (38)$$

$$I82 = 255 - G \quad (39)$$

$$I_{plan8}(i, j) = \begin{cases} 255 \text{ if } 2 \times (I81(i, j) + I82(i, j)) > 255 \\ 2 \times (I81(i, j) + I82(i, j)) \text{ Otherwise} \end{cases} \quad (40)$$

Algorithm 9:

$$I_{plan9}(i, j) = \begin{cases} 0 \text{ if } (170 - R) < 0 \\ (170 - R) \text{ Otherwise} \end{cases} \quad (41)$$

Algorithm 10:

$$I_{plan10}(i, j) = \begin{cases} 255 \text{ if } (1.6 \times B(i, j)) > 255 \\ (1.6 \times B(i, j)) \text{ Otherwise} \end{cases} \quad (41)$$

Algorithm 11:

$$I11(i, j) = \begin{cases} 255 \text{ if } 2 \times (255 - B(i, j)) > 255 \\ 2 \times (255 - B(i, j)) \text{ Otherwise} \end{cases} \quad (43)$$

$$I_{plan11} = 255 - I11 \quad (44)$$

Algorithm 12:

$$I_{plan12} = \begin{cases} 0 \text{ if } (255 - R(i, j)) - 120 < 0 \\ (255 - R(i, j)) - 120 \text{ Otherwise} \end{cases} \quad (45)$$

Algorithm 13:

$$I_{plan13} = \begin{cases} 0 \text{ if } R(i, j) - 120 < 0 \\ R(i, j) - 240 \text{ Otherwise} \end{cases} \quad (46)$$

The core equations of Algorithms 1-13 are summarized in Table 2. In certain embodiments, each Algorithm can further include inlet and peninsula removal by post processing methods described herein.

TABLE 2

The equations of Algorithms 1-13, presented in order.

| Algorithm | Equations |
|---|---|
| 1 | 9-21 |
| 2 | 9, 22-23, filtration by median filter using window size of [10, 10], 16-21 |
| 3 | 24-28, filtration by median filter using window size of [10, 10], 16-21 |
| 4 | 29, filtration by median filter using window size of [10, 10], 16-21 |
| 5 | 30-32, filtration by median filter using window size of [10, 10], 16-21 |
| 6 | 9, 33-34, 16-21 |
| 7 | 35-37, 16-21 |
| 8 | 38-40, 16-21 |
| 9 | 41, 16-21 |
| 10 | 42, 16-21 |
| 11 | 43-44, 16-21 |
| 12 | 45, 16-21 |
| 13 | 46, 16-21 |

In some embodiments, two or more of Algorithms 1-13 can be applied to a dermoscopy image. In a particular embodiment, two or more of Algorithms 1-7 can be applied to a dermoscopy image. By calculating XOR error (equation 47, below) between a manual border and each of the contours generated by the two or more algorithms, the contour having the lowest XOR for a particular dermoscopy image can be selected as a best representation of the contour for the skin lesion appearing in the image. This process can be repeated over a training set of lesions, and the border having the best characteristics over that set of lesions can be used for any new lesion or group of lesions that can comprise a test set. Furthermore, other characteristics of various areas of the original image after the border segmentation, including the area inside the border, outside the border, and over a narrow strip at the border rim, in any color plane, can be used to select which of the 13 borders is appropriate for that given image. This selection process may proceed automatically using a classifier operating upon the above characteristics to choose the most appropriate border.

Post Processing

Figure 8:
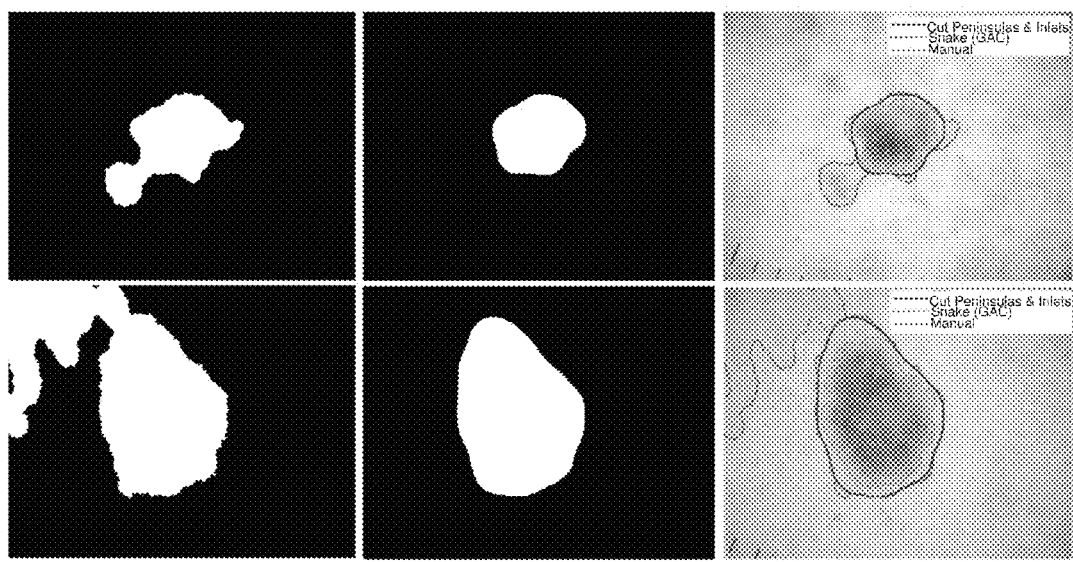
FIG. 8: Images and photographs showing examples of peninsulas being removed from the lesion: GAC mask (left panels); post processing to excise peninsula (center panels); and overlay of before and after post-processing of contour (right panels).
Figure 9:
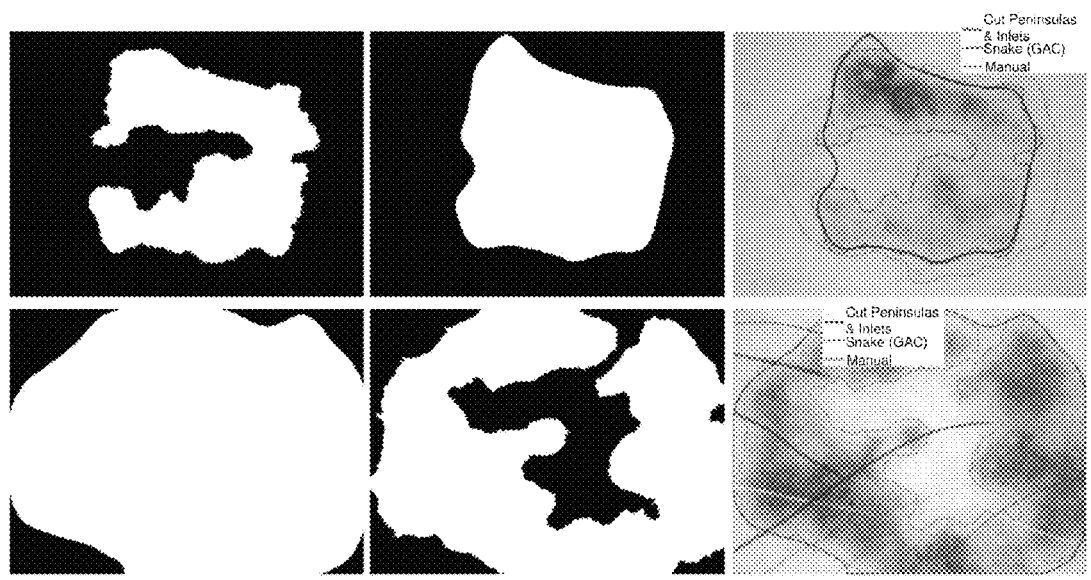
FIG. 9: Images and photographs showing examples of inlets being added to the lesion: GAC mask (left panels); post processing to fill inlet (center panels); and overlay of before and after post-processing of contour (right panels).

Occasionally, a portion of the mask protrudes out of the lesion and is connected to it by a narrow neck (peninsula), as in FIG. 8, or goes into the lesion (inlet), also separated from the background skin by a narrow neck, as in FIG. 9. Peninsulas and inlets are irregular shapes not found naturally in benign or malignant skin lesions. These nearly always represent border errors.

Identifying Peninsulas and Inlets

Figure 7:
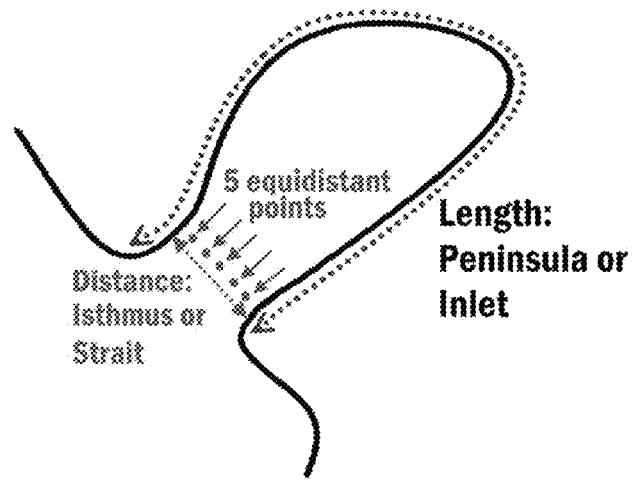
FIG. 7: Diagram demonstrating the decision of whether a detected structure is an inlet or a peninsula, wherein the position of five equidistant points just inside the structure are determined to lie within the lesion.

Inlets and peninsulas can be found by scanning the contour by segments and measuring the Euclidian distance between 2 points located within the same segment at least 5 pixels from each other (dashed red line in FIG. 7 denoted 'Distance') and determining the length along the contour between these 2 points (dashed blue line in FIG. 7). An inlet or peninsula is present if Length≥2×Distance.

Removal of Peninsulas and Filling of Inlets

The decision of whether the structure is an inlet or a peninsula can be made by placing at least one point within the inlet or peninsula structure along the Euclidian shortest distance between the two points within the segment (e.g., FIG. 7, where five equidistant points are used, although a single point, or any other number of points can also be used). Where the point(s) is within the lesion contour, the structure can be identified as a peninsula. Where the point(s) is outside the lesion contour, the structure can be identified as an inlet. When a peninsula is found, it is separated from the lesion by a morphological erosion operation using a disk structuring element with radius equal to half the isthmus distance. Finally, the largest object is dilated with the same disk, by morphological dilation.

When an inlet is found, it is added to the lesion by a morphological closing operation using a disk as a structuring element with radius equal to half the strait distance. When both peninsula and inlets are found, both of the above procedures are used. Examples of peninsulas removed from the lesion are shown in FIG. 8. Examples of inlets added to the lesion are shown in FIG. 9.

Figure 18:
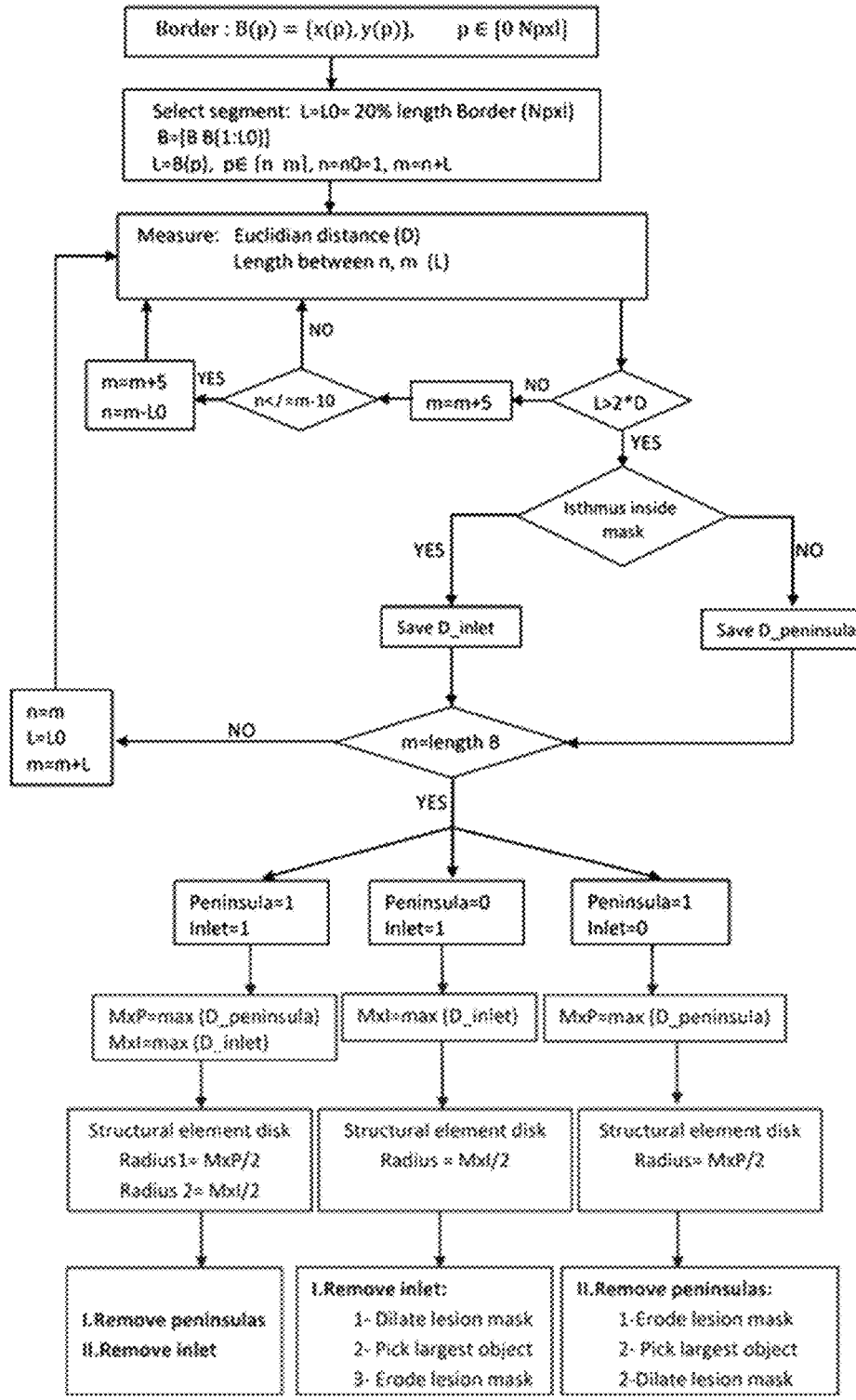
FIG. 18: Schematic representing the peninsula and inlet algorithm.
Figure 19A:
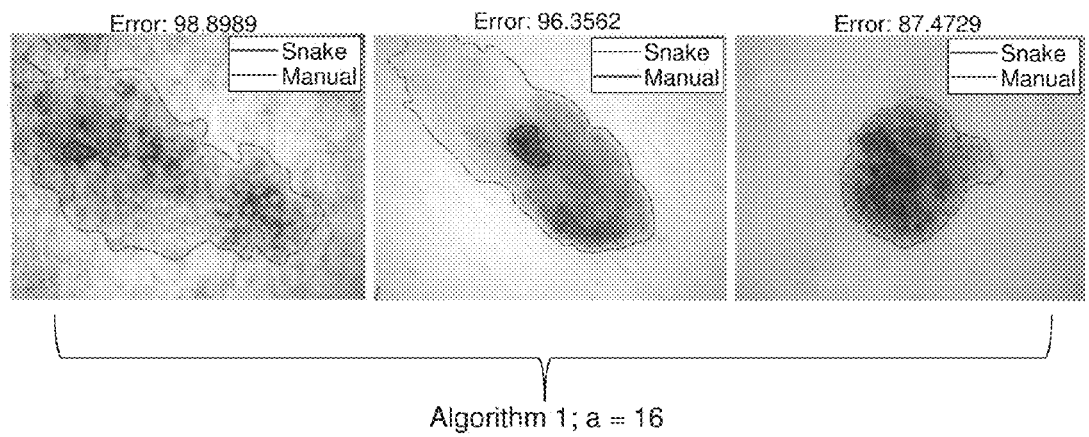
Figure 19B:
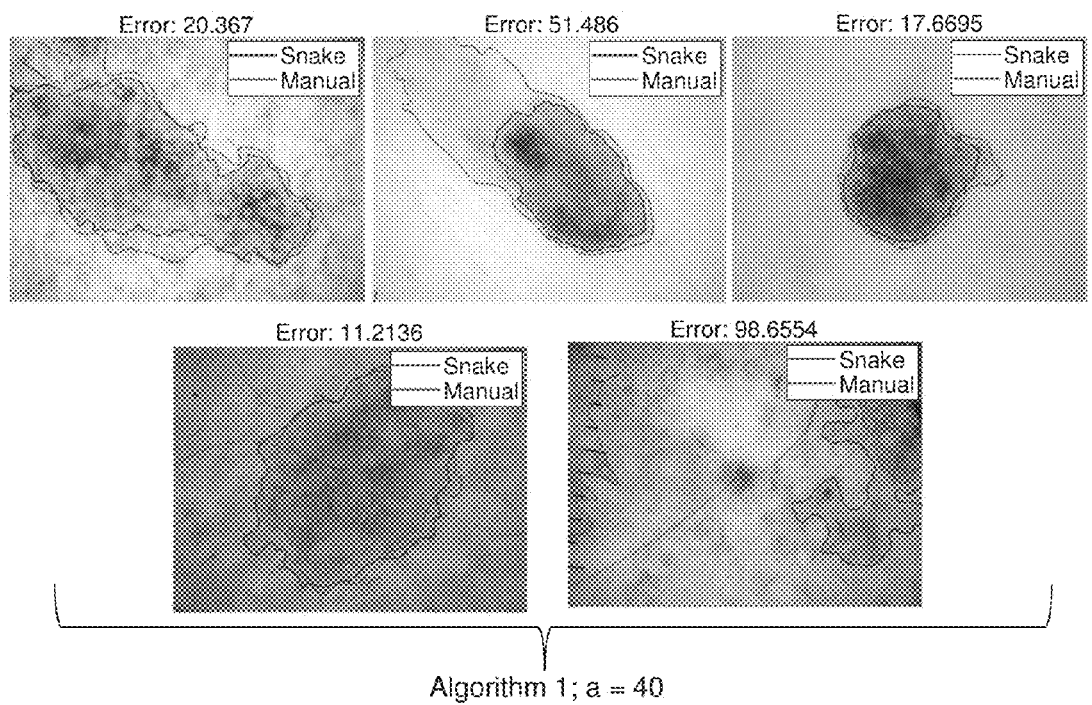
Figure 19C:
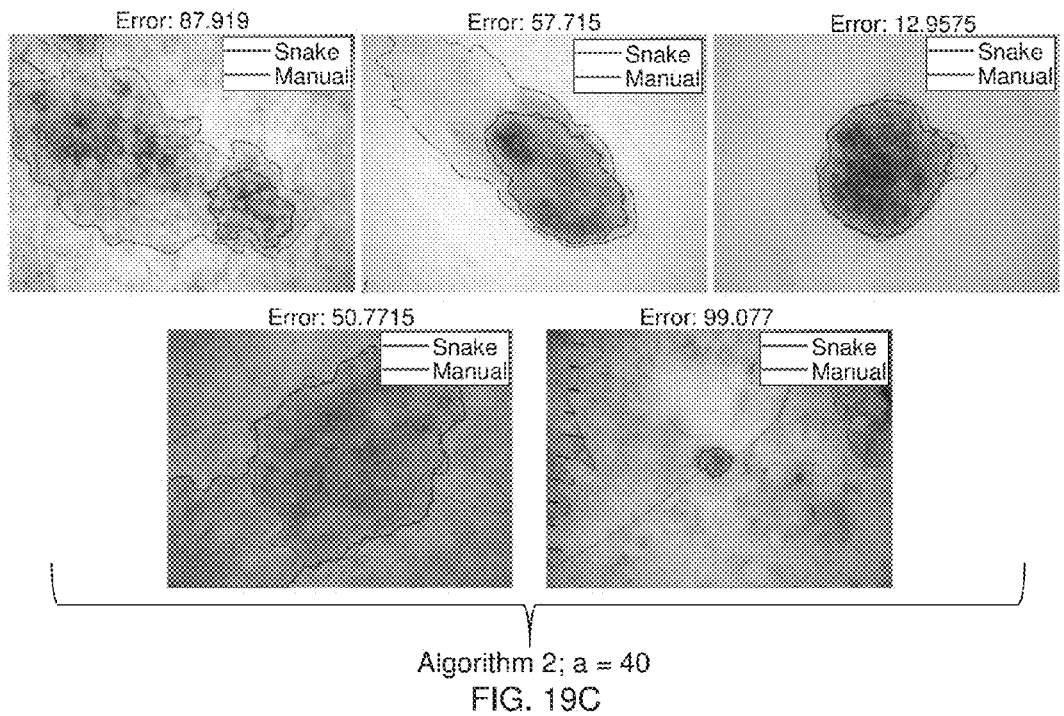
Figure 19D:
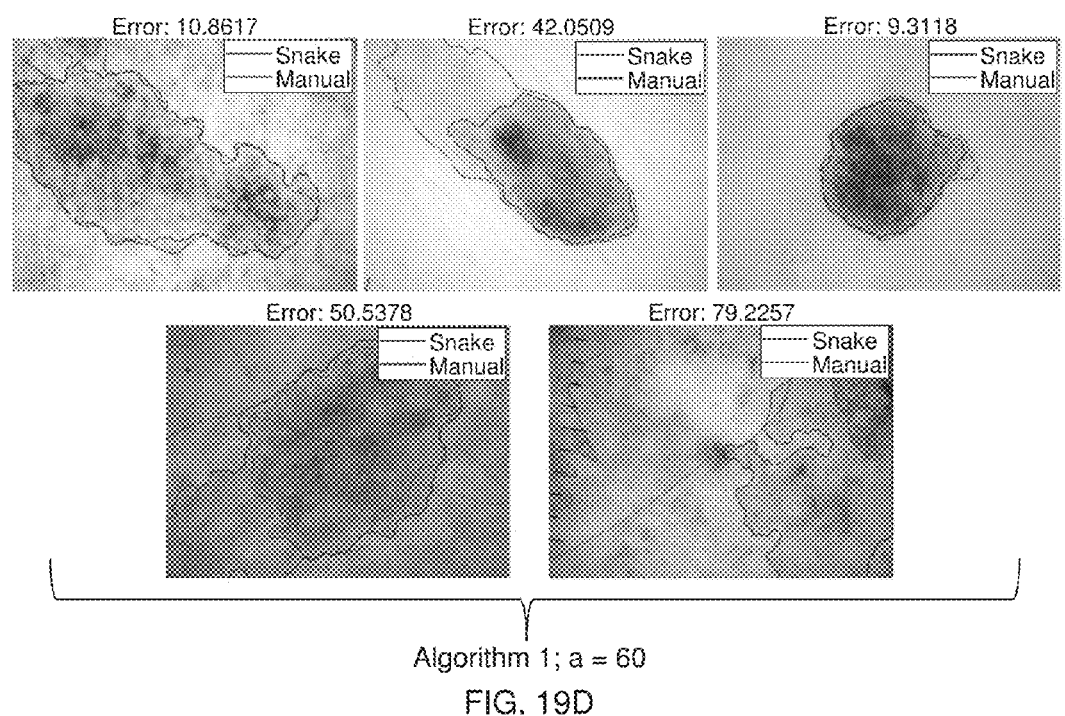
Figure 19E:
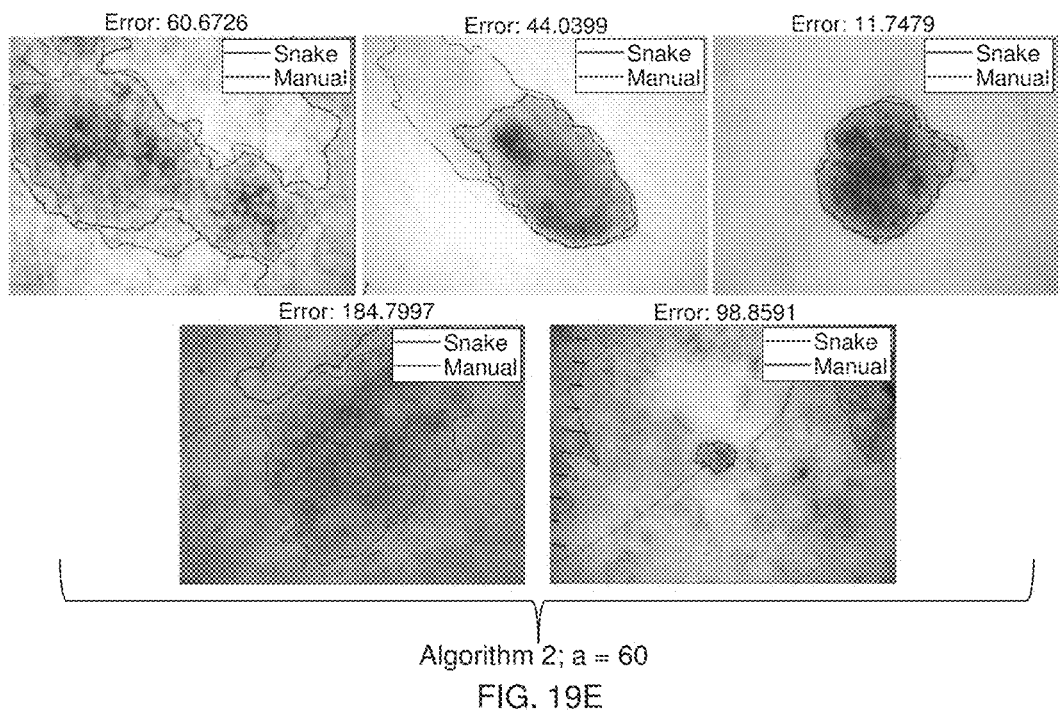
Figure 19F:
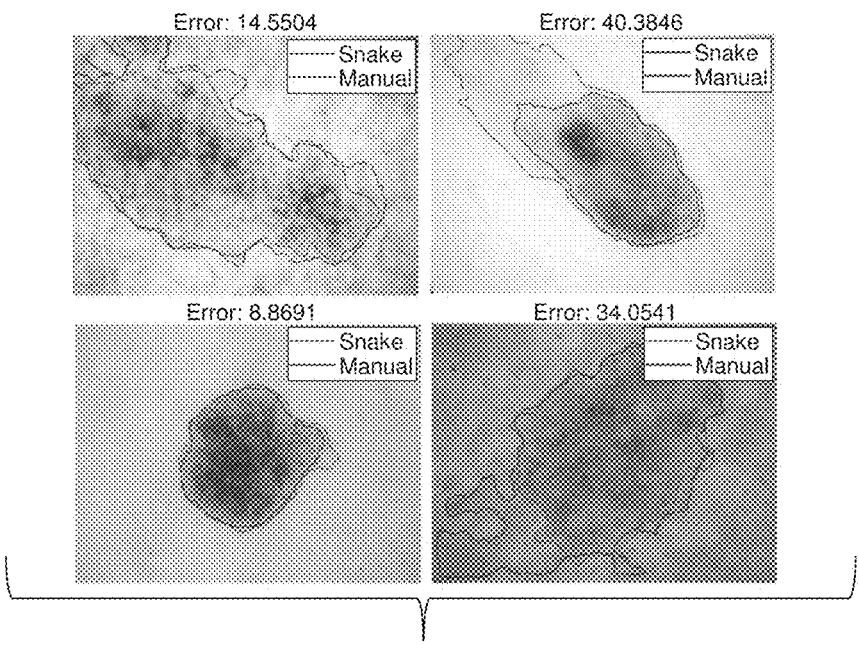
Figure 19G:
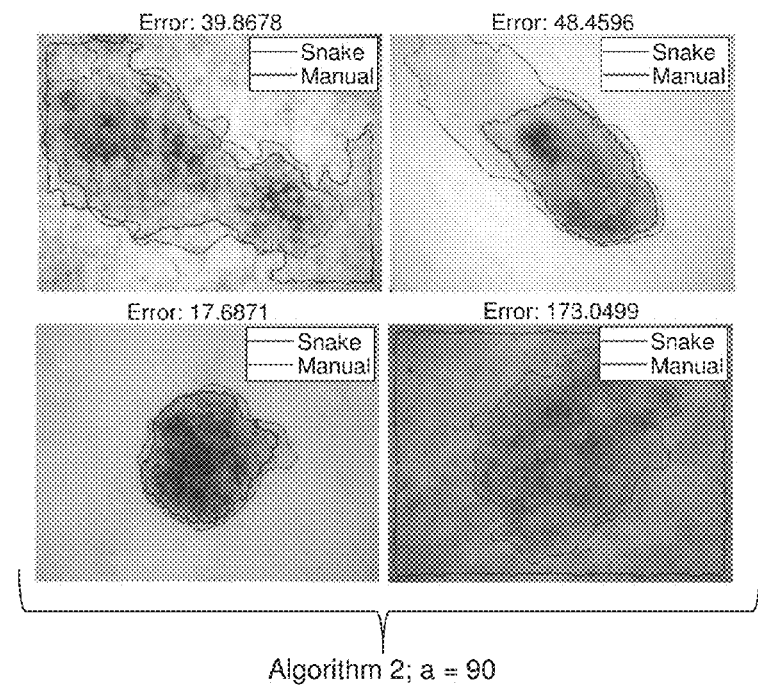
Figure 19H:
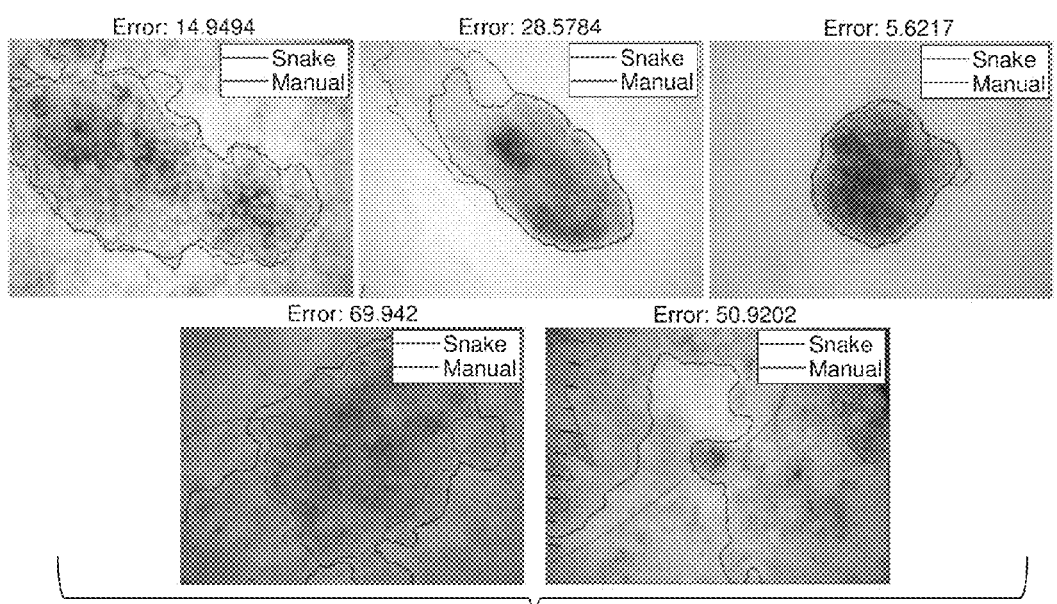
Figure 19I:
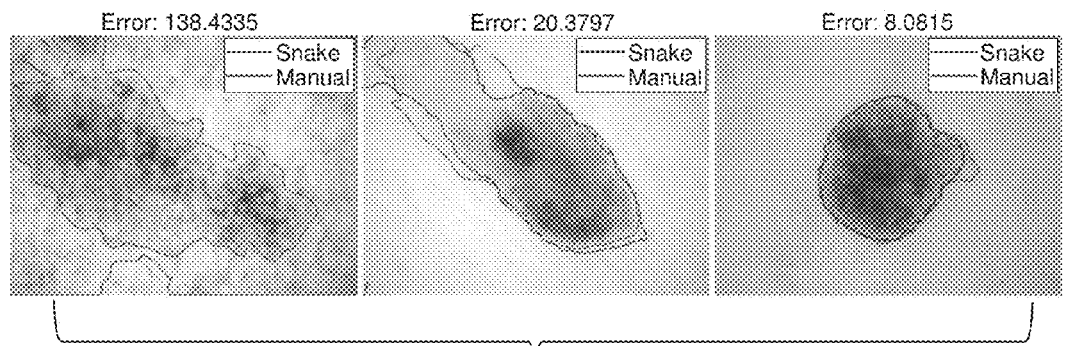
Figure 19J:
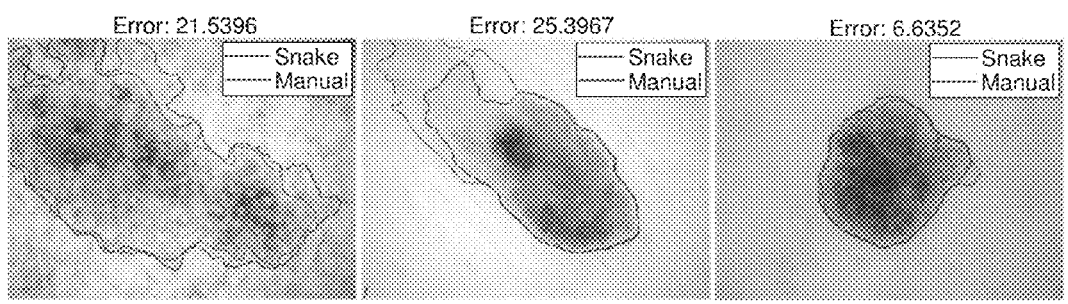
Figure 19K:
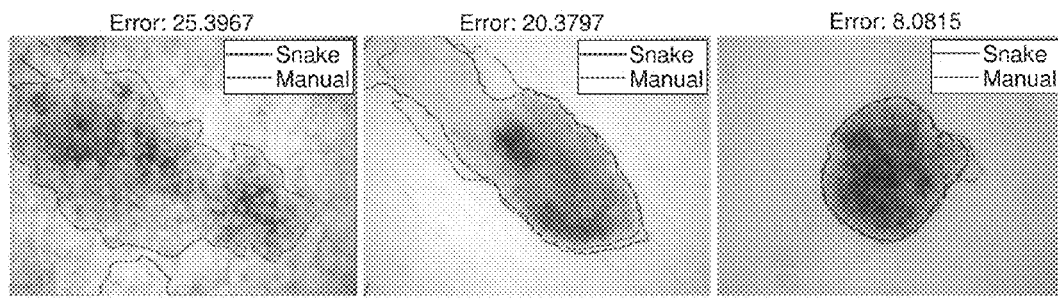
Figure 20:
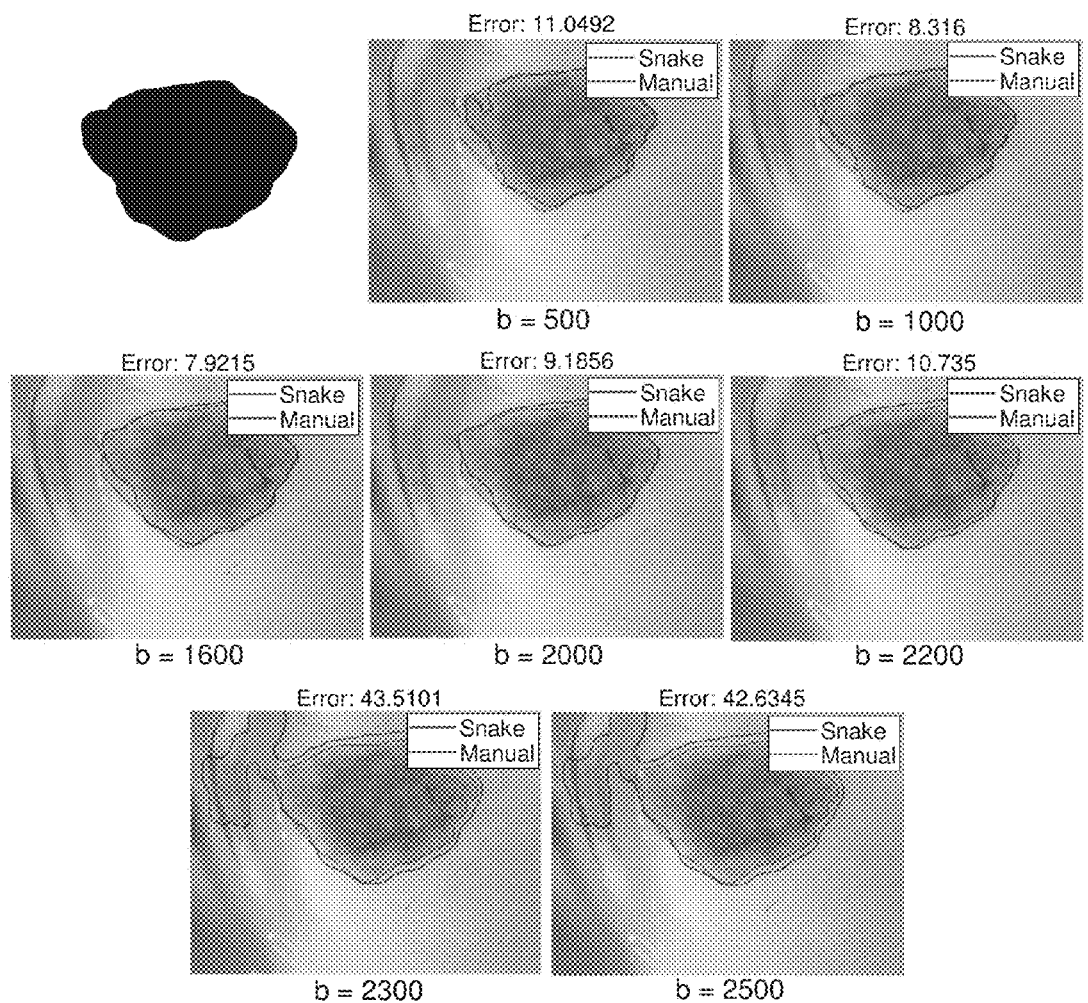
FIG. 20: Examples of border results for Algorithm 1, using different values for parameter b.

The peninsula and inlet algorithm is shown in FIG. 18.

In certain embodiments, peninsulas and/or inlets can be identified and corrected in the skin lesion contours generated by any one of Algorithm 1-13.

General Description

An active contour model (snakes) can be described as having the snakes lock onto nearby edges and localizing the edges accurately. However, noise in dermoscopy images including but not limited to hair, rulers, and ulcers often have sharp edges, and the snake contour stick on these edges rather than the lesion edge. Although the GVF snake model can have a larger capture range and better ability to find concavities than the traditional snake model, the GVF snake model remains susceptible to sticking on noisy artifacts. The methods described herein implement geometric active contours in conjunction with heavy filtration, color plane extraction, and adaptive dilation to reduce the effects of noisy artifacts and minimize or eliminate sticking. In some embodiments, the methods described herein further eliminate lesion peninsulas and inlets.

The high level of filtering and convolution, in multiple steps before and after the extraction step, enable the GAC technique described herein to effectively eliminate both primary problems encountered with contour techniques: stopping or sticking of the border at artifacts, and errors in border initialization. Even very significant noise, in the form of hair, bubbles, and/or ruler marks, is effectively eliminated. No additional hair removal software is needed. Although a number of pre-set parameters can be implemented, an automatic threshold yields an adaptable and robust algorithm. The initial border produced by the methods described herein is accurate, and the GAC border evolves very little.

The method of extraction of the blue plane from the red plane (e.g., equations 13-15) extends a spectral segmentation method wherein the difference between the red and blue plane, corresponding to the extreme ends of the visible light spectrum, best represent the coarse texture in the color image and gives the best segmentation. The use of this spectral difference can be used to show a fundamental biological property of melanin, the main pigment in the skin, for which absorption steadily increases as wavelength increases in the range from 300-100 nm. The methods described herein successively extract the blue plane and the smoothed grayscale image from the red plane. Additional biological features used here include the enlargement of the lesion area by Otsu threshold modification (equation 18), boundary smoothing, and peninsula and inlet removal.

A 100 image set reported for the GAC algorithm attained an XOR error result that was comparable to the inter-dermatologist border differences. The median GAC XOR error was 6.7%; the median between-dermatologist XOR difference was 7.4%, and the GVF snake XOR error was 14.2%. The median GAC XOR error was higher (23.9%) on the large set of images, which varied widely and included 350 basal cell carcinomas, which often lack pigment. Therefore, 12 additional border options were developed (algorithms 12-13). Choosing the option with the best border result as measured by lower XOR error, lesion by lesion, can be viewed as the theoretical lower limit of the XOR error for the ensemble of GAC borders, which yielded a median XOR border error as low as 12.1%.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this disclosure, and without departing from the spirit and scope thereof, can make various changes and modifications of the invention to adapt it to various usages and conditions.

Example 1—Comparison with GVF Snake Algorithm: XOR Border Error

Manual borders for dermoscopy images were obtained by a dermatologist selecting border points. A second-order closed curve was used to connect the manually selected points. The segmentation error between manual and automatic borders is defined here by the sum of all error pixels (pixels that are within one border and outside the other border), divided by number of pixels in the manual border:

$$XOR \text{ Error} = 100\% \times \frac{(AutoMask \cup ManualMask) - (AutoMask \cap ManualMask)}{ManualMask} \quad (47)$$
$$= 100\% \frac{(AutoMask \text{ } XOR \text{ } ManualMask)}{ManualMask}$$

where XOR denotes the exclusive OR operation. This may be stated briefly, using the notation AM=AutoMask and MM=ManualMask. Further, noting pixels in AutoMask that are outside ManualMask as FP and pixels in ManualMask that are not in AutoMask as FN, as follows:

$$XOR \text{ Error} = \frac{\text{Area}(AM \oplus MM)}{\text{Area}(MM)} = \frac{FP + FN}{TP + FN} \quad (48)$$

In another embodiment, it is possible to use different denominators to give a better relative representation of FP and FN error, by dividing the FP error by the area outside the manual mask (FP+TN), and dividing the false negative area by the area inside the manual mask (TP+FN), which serves to apply greater relative weight to lesion area missed. This is called the Relative XOR Error:

$$\text{Relative } XOR \text{ Error} = \frac{FN}{TP + FN} + \frac{FP}{FP + TN} \quad (49)$$

In automatic classification, it is more important for the border to detect most of the lesion (i.e. reduce FN) at the cost of detecting extra area outside the lesion (extra FP) than it is to detect the lesion only and no area outside the lesion (i.e. reduce FP) at the cost of more area missed inside the lesion (greater FN). Thus, considering the possible values of ω as it is allow to vary, to recognize the relative importance of FP and FN values for the modified XOR error, co should be less than 0.5.

$$\text{Weighted } XOR \text{ Error} = (1 - \omega)\left(\frac{FN}{FN + TP}\right) + \omega\left(\frac{FP}{FP + TN}\right) \quad (50)$$

where in some embodiments, ω is optimized to 0.3334.

Figure 10:
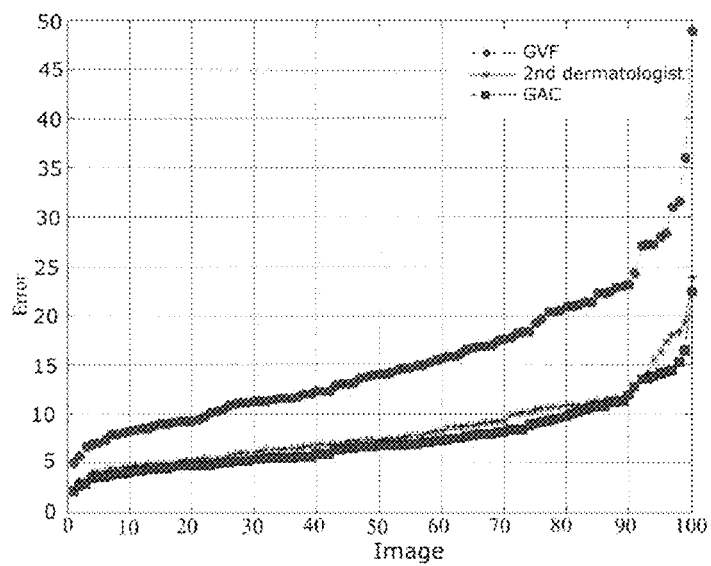
FIG. 10: Graph showing sorted XOR errors for 100 images: GVF error; GAC error; and between-expert difference ($2^{nd}$ dermatologist).

An implementation of the gradient vector field contour technique (GVF snake) on 100 dermoscopy pigmented lesion images: 30 melanomas and 70 benign images, and reported the XOR error on each image and the XOR difference between the first and second expert dermatologist borders. Algorithm 1 (equations 9-20), followed by convolving with filter H2 (equation 14), generation of $I_{newsth}$ (equation 15), and contour initialization (equations 16-21) were applied to the same 100 images without training on this set. XOR error with the manual border was computed. The three XOR errors (GVF, between-expert difference, and (GAC) are plotted together in ascending error order in FIG. 10 for all 100 images. The median XOR errors shown in Table 3 are 14.2% for GVF snake border, 7.4% for between-expert differences, and 6.7% for GAC border.

TABLE 3

Median, average, and standard deviation of XOR errors for
100 images. XOR error is shown for GVF and GAC
techniques as well as the inter-dermatologist XOR difference

|  | GVF (%) | 2nd dermatologist (%) | GAC (%) |
| --- | --- | --- | --- |
| Median | 14.2 | 7.4 | 6.7 |
| Average | 15.6 | 8.4 | 7.5 |
| SD | 7.2 | 3.8 | 3.4 |

GCF, gradient vector flow;
GAC, geodesic active contour.

Figure 11:
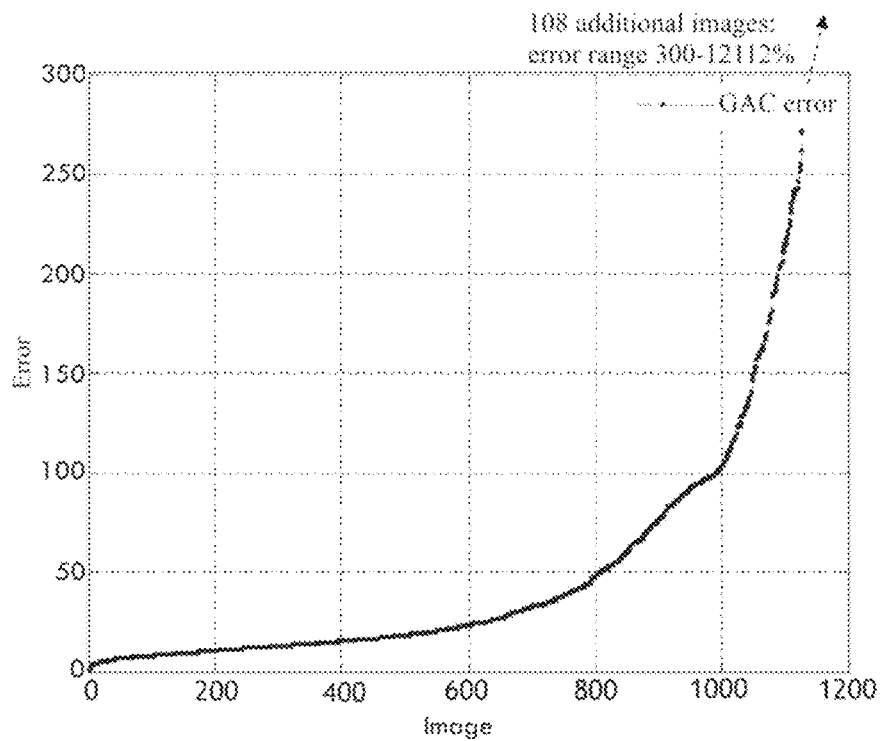
FIG. 11: Graph showing sorted GAC XOR border errors between manual and GAC results for set of 1130 images.

Example 2—XOR Border Error on 1238 Pigmented and Non-Pigmented Dermoscopy Images The set of 100 pigmented lesion images used in Example 1 had clear borders, without the difficulties of noise and low-contrast depicted in FIG. 1. A set of 1238 lesion images from four dermatology clinics was tested for border determination as described in Example 1. This set included both pigmented lesions (n=888) and hypopigmented basal cell carcinomas with difficult borders (n=350). XOR border error results between manual and GAC results are shown in Table 4 and FIG. 11.

TABLE 4

Average, median, and standard deviation of XOR error for 1238
images and for 1237 images (without tiny lesion for which a
larger border was found. The XOR error was 5433%

|  | 1238 images (%) | 1130 images (%) |
| --- | --- | --- |
| Median | 23.9 | 21.0 |
| Average | 131.5 | 45.8 |
| SD | 523.9 | 54.1 |

Figure 12:
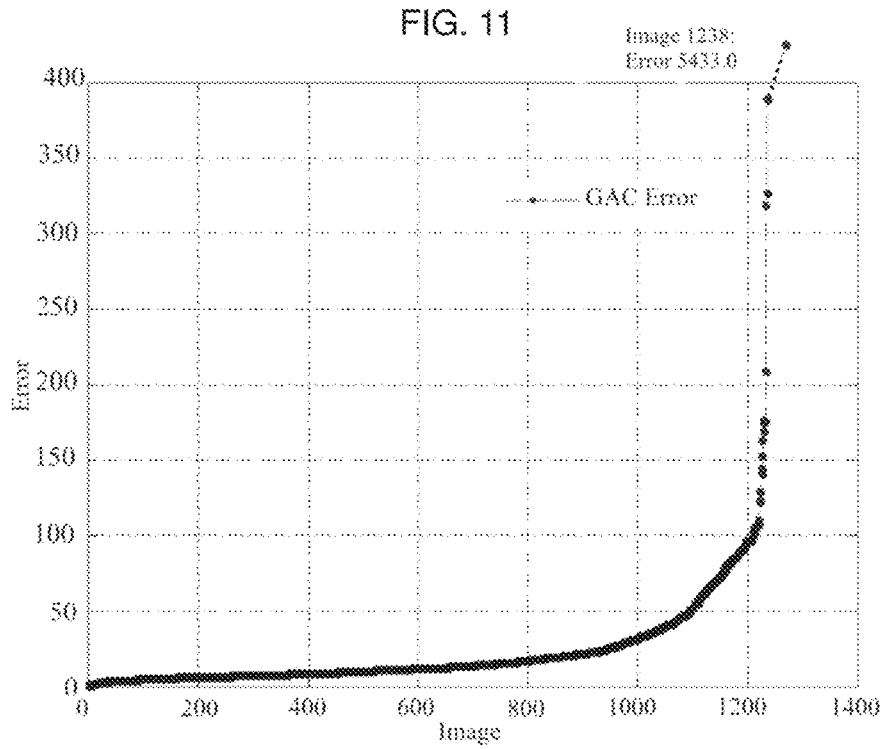
FIG. 12: Graph showing sorted GAC XOR border errors for 1238 images, using best of 13 border transformation options for each image.

Example 3—Results on 1238 Pigmented and Non-Pigmented Dermoscopy Images for Lowest-Error Choice of 13 GAC Transformations The basic GAC algorithm (Algorithm 1; equations 9-21) may result in errors on difficult lesions. Because a single set of parameters to optimize borders for varied lesions is not possible, twelve image transformations (Algorithms 2-13) were developed to replace equations 9-15 of Algorithm 1 (see Table 2). FIG. 12 and Table 5 show results using the GAC algorithm with lowest XOR error for each image of the 13 GAC algorithms. Using this lowest-error choice in each instance represents a lower-error bound on the multiple-choice GAC technique.

TABLE 5

Average, median, and standard deviation of XOR error for 1238
images and for 1237 images, using the automatic border method
with the lowest XOR difference from the manual border (without
tiny lesion for which border error was 5433%)

|  | 1238 images (%) | 1237 images (%) |
| --- | --- | --- |
| Median | 12.1 | 12.1 |
| Average | 27.3 | 22.9 |
| SD | 156.7 | 30.4 |

Example 4—Primary GAC Algorithm Results

Figure 13:
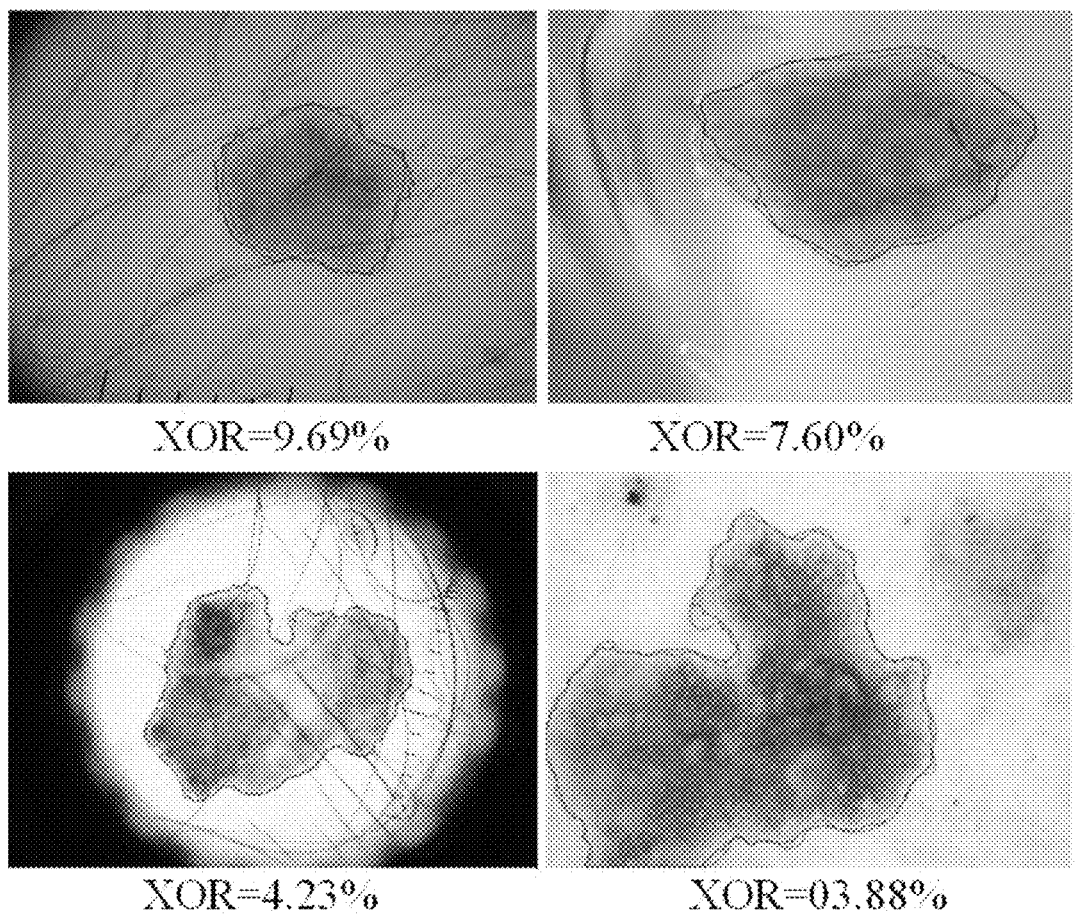
FIG. 13: Photographs showing segmentation in different types of lesions, with XOR errors of less than 10%. Manual borders are shown in red; automatic borders are shown in blue.

FIG. 13 shows segmentation in different types of lesions. Even on images with noise such as hair, rulers, bubble edges, and zoom artifacts, the XOR errors were less than 10%.

Figure 14:
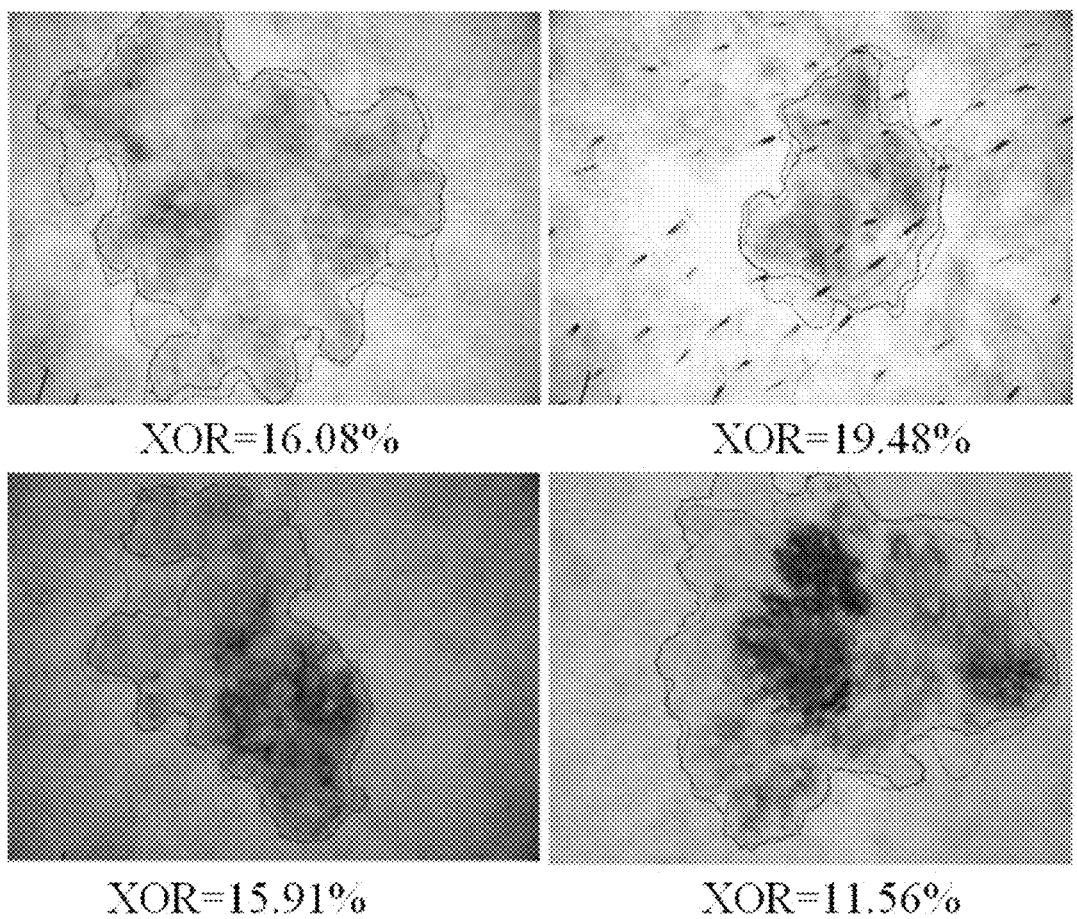
FIG. 14: Photographs showing segmentation in different types of lesions, with XOR errors of 10-20%. Manual borders are shown in red; automatic borders are shown in blue.
Figure 15:
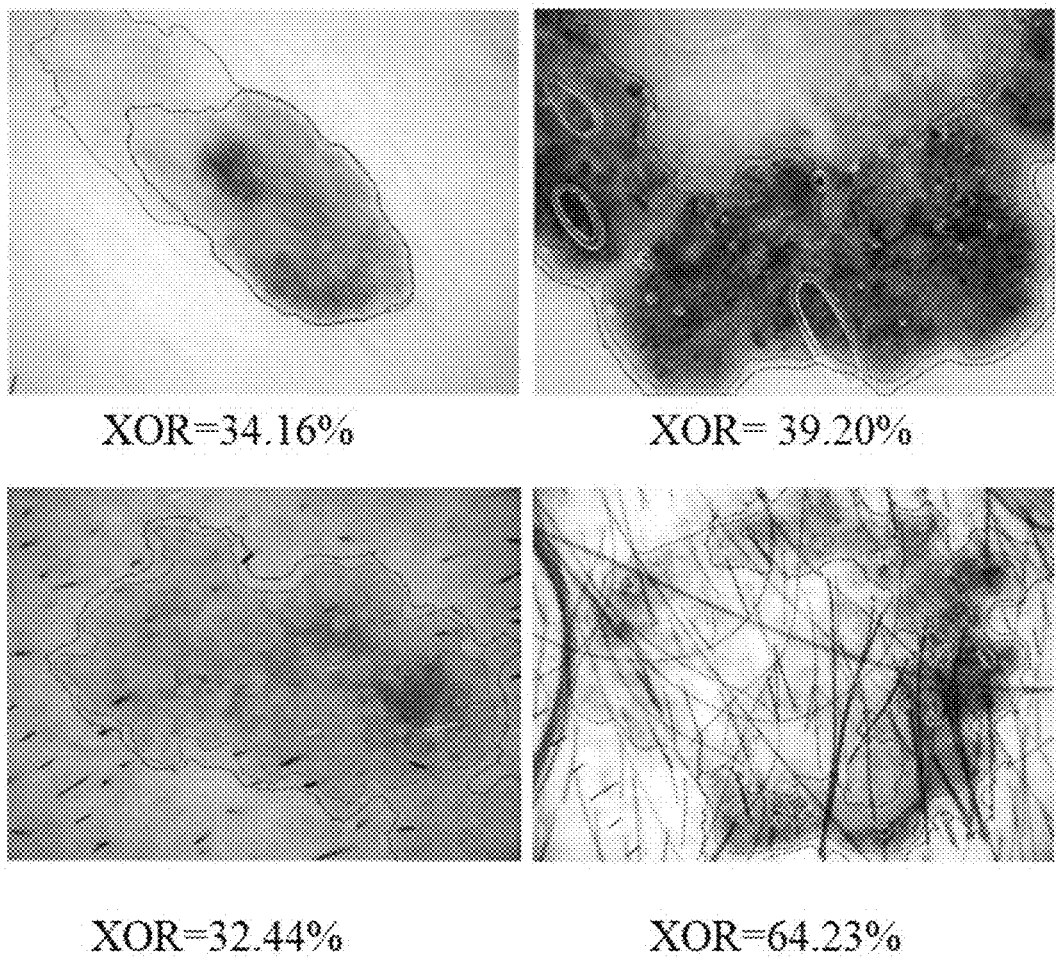
FIG. 15: Photographs showing segmentation in different types of lesions, with XOR errors of 20-30%. Manual borders are shown in red; automatic borders are shown in blue.

FIGS. 14-15 show images where the segmentation errors were 10-20% and 20-30%, respectively. For these images, the location of the manual border (red) is not obvious.

Figure 16:
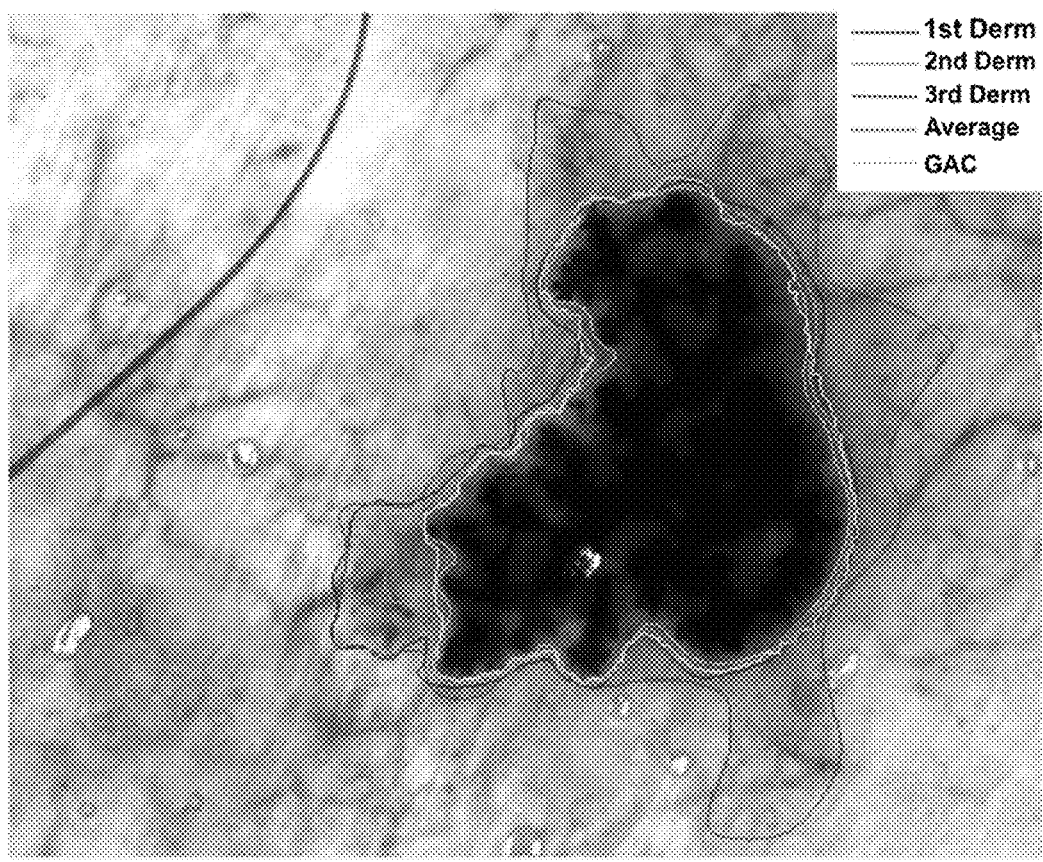
FIG. 16: Photograph showing borders from three dermatologists, the average of their borders, and the GAC automatic border.

It was found that dermatologists have a tendency to include more or less area in their border detection, as shown in FIG. 16. Compared to the first dermatologist (blue border), the second dermatologist (teal border) found on average about 1% less lesion area, and the third dermatologist (red border) found on average 4.7% larger lesion area. The GAC border (yellow border) found less area than any of the dermatologists. It found on average 0.3% less lesion area than the second dermatologist and was within the standard deviation of the three dermatologists (Table 6).

TABLE 6

Comparison of average and median area of 100 images segmented
by three dermatologists' borders, the average of their borders,
and the GAC automatic border

| Border of: | 1st derm. | 2nd derm. | 3rd derm. | Average | GAC |
| --- | --- | --- | --- | --- | --- |
| Average | 219.1 | 217.1 | 229.6 | 221.0 ± 6.7 | 216.8 |
| Median | 191.2 | 195.6 | 205.4 | 197.4 ± 7.3 | 187.0 |

Various embodiments of the disclosed subject matter may be implemented using a system and/or device that includes one or more computing devices. A computing device may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "general-purpose graphics processing units (GPGPUs)," and the like, all of which are contemplated within the scope of the subject matter disclosed herein. In embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The I/O component may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus may be one or more busses (such as, for example, an address bus, data bus, or combination thereof). The processor may be, or include, a processing device (e.g., a hardware processor, a microprocessor, etc.), a virtual processor, application specific logic hardware including, but not limited to, an Application Specific Integrated Circuit (ASIC) or a Field Programmable Gate Array (FPGA), and/or the like. Similarly, in embodiments, the computing device may include a number of processors, a number of memory components, a number of I/O ports, a number of I/O components, and/or a number of power supplies. Additionally any number of these components, or combinations thereof, may be distributed, virtualized, and/or duplicated across a number of computing devices. In embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like.

In embodiments, the memory stores computer-executable instructions for causing the processor to implement aspects of embodiments of system components discussed herein and/or to perform aspects of embodiments of methods and procedures discussed herein. The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

An embodiment may be recognized as a lesion segmentation computer system implementing the processes of the above described lesion segmentation method. Further, in describing the lesion segmentation computer system one or more individual processes described above for the lesion segmentation method may be broken down and represented as a subsystem of the overall lesion segmentation computer system. A subsystem of the lesion segmentation computer system may be assigned, in whole or in part, to a particular hardware implemented system, such as a dedicated Application Specific Integrated Circuit (ASIC) or Field Programmable Gate Array (FPGA). One or more subsystems, in whole or in part, may alternatively be implemented as software or firmware instructions defining the operation of a computer system with specific regard to the one or more subsystems implemented as software or firmware instructions. The software or firmware instructions may cause the Central Processing Unit, memory, and/or other systems of a computer system to operate in particular accordance with the particular one or more subsystems designated features. Furthermore, various embodiments of the present invention may further provide alternate choices for segmentation, proving advantageous for computing optimal segmentation choices for the wide variety of lesions encountered in practice While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiments disclosed herein contemplated for carrying out this invention, but that the invention will include all embodiments falling within the scope of the claims.

The invention claimed is:

1. A lesion segmentation method performed on a computer system that automatically finds a border of a lesion shown in a digital image based on a grayscale image comprising a grayscale version of the digital image and on a Red-Green-Blue (RGB) color image comprising an RGB component color version of the digital image, the method comprising:
   smoothing the grayscale image by convolving the grayscale image with a first spatial filter to generate a smoothed grayscale image;
   generating an extracted image by subtracting a value of each pixel of a blue component plane of the RGB color image from each corresponding pixel value of a red component plane of the RGB color image and assigning a pixel value of 0 if the subtraction results in a negative number, wherein the extracted image is a result for each corresponding pixel value of the extracted image;
   generating a new image by subtracting a value of each pixel of the smoothed grayscale image from each corresponding pixel value of the extracted image and assigning a pixel value of 0 if the subtraction results in a negative number, wherein the new image is a result for each corresponding pixel value of the new image;
   smoothing the new image by convolving the new image with a second spatial filter to generate a smoothed new image;
   binarizing the smoothed new image to generate a black and white image; and
   constructing the border of the lesion as a contour of a pixel width edge between black portions and white portions of the black and white image.

2. The lesion segmentation method of claim 1, wherein:
   the first spatial filter comprises a 4×4 spatial filter with a first constant multiplier value, the first constant multiplier value comprising a value that is greater than or equal to $\frac{1}{130}$ and that is less than or equal to $\frac{1}{40}$; and
   the second spatial filter comprises a 10×10 spatial filter with a second constant multiplier value, the second constant multiplier value comprising a value that is greater than or equal to $\frac{1}{2500}$ and that is less than or equal to $\frac{1}{100}$.

3. The lesion segmentation method of claim 1, further comprising generating the RGB color image from a supplied digital color image of the lesion.

4. The lesion segmentation method of claim 1, further comprising generating the grayscale image by averaging each pixel value of the red component plane, a green component plane, and the blue component plane of the RGB color image as a result for each corresponding pixel value of the grayscale image.

5. The lesion segmentation method of claim 1, further comprising generating the grayscale image by adding together 0.2989 multiplied times the red component plane pixel value with 0.5870 multiplied times a green component plane pixel value and with 0.1140 multiplied times the blue component plane pixel value of the RGB color image as a result for each corresponding pixel value of the grayscale image.

6. The lesion segmentation method of claim 1, further comprising, before the step of binarizing the smoothed new image to generate the black and white image:
   smoothing the smoothed new image using a first median filter to generate a further smoothed new image; and smoothing the further smoothed new image by convolving the further smoothed new image with a third spatial filter to generate a still further smoothed new image; and wherein the step of binarizing the smoothed new image to generate the black and white image comprises binarizing the still further smoothed new image.

7. The lesion segmentation method of claim 6, wherein:
the first median filter is a 30×30 median filter; and
the third spatial filter is a 40×40 spatial filter with a third constant multiplier value, the third constant multiplier value comprising a value that is greater than or equal to $1/2200$ and that is less than or equal to $1/1000$.

8. The lesion segmentation method of claim 1, further comprising, before the step of binarizing the smoothed new image to generate the black and white image, expanding the lesion shown in the smoothed new image by reducing an Otsu threshold by 10, or by setting the Otsu threshold to $2.2204 \times 10^{-16}$ when reducing the Otsu threshold by 10 results in a negative value, such that the Otsu threshold is used as the threshold value for the step of binarizing the smoothed new image.

9. The lesion segmentation method of claim 1, further comprising, before the process of constructing the border of the lesion:
selecting an object from at least one object appearing in the black and white image as the lesion, wherein the selected object is the most central object;
filling in the selected object representing the lesion to remove any holes in the selected object representing the lesion; and
performing dilation of mathematical morphology to remove extraneous objects other than the selected object representing the lesion to generate a black and white image of the lesion.

10. The lesion segmentation method of claim 1, further comprising:
scanning the contour of the lesion by segments;
measuring a Euclidian shortest distance between each two points of each segment of the contour of the lesion, where each two points of the segment are separated by at least a predetermined number of pixels along the contour of the lesion;
determining a length along the contour between each two points of each segment of the contour of the lesion;
comparing the Euclidian shortest distance and the length along the contour between each two points of each segment of the contour of the lesion; and
determining that an inlet or peninsula structure is present when the length along the contour between each two points of each segment is greater than or equal to twice the Euclidian shortest distance between each two points of each segment.

11. The lesion segmentation method of claim 10, wherein said predetermined number of pixels along the contour of the lesion is between 5 and 10 pixels.

12. The lesion segmentation method of claim 10, further comprising:
placing at least one point within the inlet or peninsula structure of the lesion along the Euclidian shortest distance between each two points of each segment determined to be the inlet or peninsula structure;
determining that the inlet or peninsula structure is a peninsula when the at least one point within the inlet or peninsula structure is within the contour of the lesion; and separating the peninsula from the contour of the lesion using a morphological erosion operation.

13. The lesion segmentation method of claim 10, further comprising:
placing at least one point within the inlet or peninsula structure of the lesion along the Euclidian shortest distance between each two points of each segment determined to be the inlet or peninsula structure;
determining that the inlet or peninsula structure is an inlet when the at least one point within the inlet or peninsula structure is outside the contour of the lesion; and
adding the inlet within the contour of the lesion using a morphological closing operation.

14. The lesion segmentation method of claim 1, further comprising generating at least one alternate border based on the grayscale image and the RGB color image.

15. The lesion segmentation method of claim 14, wherein the method of claim 11 is performed on each alternate border and wherein any present inlet is added to the contour of the lesion and any present peninsula is separated from the contour of the lesion.

16. The lesion segmentation method of claim 14, wherein the at least one alternate border is generated by at least one method selected from:

(a) Algorithm 2, wherein Algorithm 2 comprises convolving the grayscale image (IG) with the first spatial filter to generate the smoothed grayscale image, IGsth, and determining $I_{plan2}$, wherein $$I_{plan2} = (255 - IG2) + \frac{1}{3} \times IG2,$$

$$\text{and wherein } IG2 = \begin{cases} 255 & \text{if } 5 \times IGsth > 255 \\ 5 \times IGsth & \text{otherwise} \end{cases};$$

filtering $I_{plan2}$ by using a median filter having a window size of [10,10];
binarizing the filtered $I_{plan2}$ to generate a black and white image; and
constructing the at least one alternate border of the lesion as a contour of a pixel width edge between black portions and white portions of the black and white image;

(b) Algorithm 3, wherein Algorithm 3 comprises convolving the grayscale image (IG) with a third spatial filter, H4, wherein $$H4 = \frac{1}{45} \times \begin{bmatrix} 1 & 1 & 1 & 1 \\ 1 & 1 & 1 & 1 \\ 1 & 1 & 1 & 1 \\ 1 & 1 & 1 & 1 \end{bmatrix},$$

to generate a smoothed grayscale image $IG_3$;
determining $I_{plan3}$, wherein $I_{plan3}=IG32$, wherein $$IG31(i, j) = \begin{cases} 0 & \text{if } (R(i, j) - B(i, j)) < 0 \\ (R(i, j) - B(i, j)) & \text{Otherwise} \end{cases},$$

and wherein $$IG32(i, j) = \begin{cases} 0 \text{ if } (IG31(i,j) - IG3(i,j)) < 0 \\ (IG31(i,j) - IG3(i,j)) \text{ Otherwise} \end{cases}$$

filtering $I_{plan3}$ by using a median filter having a window size of [10,10];

binarizing the filtered $I_{plan3}$ to generate a black and white image; and constructing the at least one alternate border of the lesion as a contour of a pixel width edge between black portions and white portions of the black and white image;

(c) Algorithm 4, wherein Algorithm 4 comprises determining $I_{plan4}$, wherein $$I_{plan4}(i,j) = \begin{cases} 0 \text{ if } 50*(255 - B(i,j)) > 70 \\ 50*(255 - B(i,j)) \text{ if } 50*(255 - B(i,j)) > 70 \end{cases};$$

filtering $I_{plan4}$ by using a median filter having a window size of [10,10];

binarizing the filtered $I_{plan4}$ to generate a black and white image; and constructing the at least one alternate border of the lesion as a contour of a pixel width edge between black portions and white portions of the black and white image;

(d) Algorithm 5, wherein Algorithm 5 comprises determining $I_{plan5}$, wherein $$I_{plan5}(i,j) = \begin{cases} 255 \text{ if } (255 - IG5(i,j))^2 > 255 \\ (255 - IG5(i,j))^2 \text{ Otherwise} \end{cases},$$

and wherein $$IG5(i,j) = \begin{cases} 255 \text{ if } (255 - R(i,j)) + G(i,j) > 255 \\ 255 - R(i,j) + G(i,j) \text{ Otherwise} \end{cases};$$

filtering $I_{plan5}$ by using a median filter having a window size of [10,10];

binarizing the filtered $I_{plan5}$ to generate a black and white image; and constructing the at least one alternate border of the lesion as a contour of a pixel width edge between black portions and white portions of the black and white image;

(e) Algorithm 6, wherein Algorithm 6 comprises convolving the grayscale image (IG) with the first spatial filter, H1, to generate a smoothed grayscale image IG6;

extracting the blue plane from IG6 to determine $I_{plan6}$, wherein $$I_{plan6}(i,j) = \begin{cases} 0 \text{ if } ((255 - IG6(i,j)) - B) < 0 \\ ((255 - IG6(i,j)) - B) \text{ Otherwise} \end{cases};$$

binarizing $I_{plan6}$ to generate a black and white image; and constructing the at least one alternate border of the lesion as a contour of a pixel width edge between black portions and white portions of the black and white image;

(f) Algorithm 7, wherein Algorithm 7 comprises convolving the grayscale image (IG) with a fourth spatial filter, H5, wherein $$H5 = \frac{1}{40} \times \begin{bmatrix} 1 & 1 & 1 & 1 \\ 1 & 1 & 1 & 1 \\ 1 & 1 & 1 & 1 \\ 1 & 1 & 1 & 1 \end{bmatrix},$$

to generate a smoothed grayscale image IG7;

extracting the blue plane from IG7 to determine $I_{plan7}$ wherein $$I_{plan7}(i,j) = \begin{cases} 0 \text{ if } ((255 - IG7(i,j)) - B) < 0 \\ ((255 - IG7(i,j)) - B) \text{ Otherwise} \end{cases};$$

binarizing $I_{plan7}$ to generate a black and white image; and constructing the at least one alternate border of the lesion as a contour of a pixel width edge between black portions and white portions of the black and white image;

(g) Algorithm 9, wherein Algorithm 9 comprises determining $I_{plan9}$, wherein $$I_{plan9}(i,j) = \begin{cases} 0 \text{ if } (170 - R) < 0 \\ (170 - R) \text{ Otherwise} \end{cases};$$

binarizing $I_{plan9}$ to generate a black and white image; and constructing the at least one alternate border of the lesion as a contour of a pixel width edge between black portions and white portions of the black and white image; and (h) Algorithm 12, wherein Algorithm 12 comprises determining $I_{plan12}$, wherein $$Iplan12 = \begin{cases} 0 \text{ if } ((255 - R(i,j)) - 120 < 0 \\ ((255 - R(i,j)) - 120 \text{ Otherwise} \end{cases};$$

binarizing $I_{plan12}$ to generate a black and white image; and constructing the at least one alternate border of the lesion as a contour of a pixel width edge between black portions and white portions of the black and white image.

17. The lesion segmentation method of claim 14, further comprising selecting a border of best representation for the lesion.

18. The lesion segmentation method of claim 17, wherein selecting a border of best representation for the lesion comprises determining XOR error for each border and selecting a border having a lowest XOR error value.

19. A system for lesion segmentation that automatically finds a border of a lesion shown in a digital image based on a grayscale image comprising a grayscale version of the digital image and on a Red-Green-Blue (RGB) color image comprising an RGB component color version of the digital image, the system comprising:
- a processor; and
- a memory comprising one or more computer-readable media having computer-executable instructions embodied thereon, wherein, when executed by the processor, the computer-executable instructions cause the processor to perform a method, the method comprising:
  - smoothing the grayscale image by convolving the grayscale image with a first spatial filter to generate a smoothed grayscale image;
  - generating an extracted image by subtracting a value of each pixel of a blue component plane of the RGB color image from each corresponding pixel value of a red component plane of the RGB color image and assigning a pixel value of 0 if the subtraction results in a negative number, wherein the extracted image is a result for each corresponding pixel value of the extracted image;
  - generating a new image by subtracting a value of each pixel of the smoothed grayscale image from each corresponding pixel value of the extracted image and assigning a pixel value of 0 if the subtraction results in a negative number, wherein the new image is a result for each corresponding pixel value of the new image;
  - smoothing the new image by convolving the new image with a second spatial filter to generate a smoothed new image;
  - binarizing the smoothed new image to generate a black and white image; and
  - constructing the border of the lesion as a contour of a pixel width edge between black portions and white portions of the black and white image.

20. One or more non-transitory computer-readable media having computer-executable instructions embodied thereon for lesion segmentation that automatically finds a border of a lesion shown in a digital image based on a grayscale image comprising a grayscale version of the digital image and on a Red-Green-Blue (RGB) color image comprising an RGB component color version of the digital image, wherein, when executed by a processor, the computer-executable instructions cause the processor to perform a method, the method comprising:
- smoothing the grayscale image by convolving the grayscale image with a first spatial filter to generate a smoothed grayscale image;
- generating an extracted image by subtracting a value of each pixel of a blue component plane of the RGB color image from each corresponding pixel value of a red component plane of the RGB color image and assigning a pixel value of 0 if the subtraction results in a negative number, wherein the extracted image is a result for each corresponding pixel value of the extracted image;
- generating a new image by subtracting a value of each pixel of the smoothed grayscale image from each corresponding pixel value of the extracted image and assigning a pixel value of 0 if the subtraction results in a negative number, wherein the new image is a result for each corresponding pixel value of the new image;
- smoothing the new image by convolving the new image with a second spatial filter to generate a smoothed new image;
- binarizing the smoothed new image to generate a black and white image; and
- constructing the border of the lesion as a contour of a pixel width edge between black portions and white portions of the black and white image.

* * * * *

UNITED STATES PATENT AND TRADEMARK OFFICE
CERTIFICATE OF CORRECTION

PATENT NO. : 10,229,492 B2
APPLICATION NO. : 15/231538
DATED : March 12, 2019
INVENTOR(S) : Reda Kasmi It is certified that error appears in the above-identified patent and that said Letters Patent is hereby corrected as shown below:

In the Claims

In Column 22, Line 19, in Claim 15, delete "11" and insert -- 10 --

Signed and Sealed this
Fourth Day of June, 2019

Andrei Iancu
*Director of the United States Patent and Trademark Office*